US010638927B1

(12) United States Patent
Beard et al.

(10) Patent No.: US 10,638,927 B1
(45) Date of Patent: May 5, 2020

(54) INTELLIGENT, ADDITIVELY-MANUFACTURED OUTERWEAR AND METHODS OF MANUFACTURING THEREOF

(71) Applicant: CASCA DESIGNS INC., Vancouver (CA)

(72) Inventors: Lucy A. Beard, Chattanooga, TN (US); Nigel P. Beard, Chattanooga, TN (US)

(73) Assignee: CASCA DESIGNS INC., Vancouver (CA)

( * ) Notice: Subject to any disclaimer, the term of this patent is extended or adjusted under 35 U.S.C. 154(b) by 842 days.

(21) Appl. No.: 14/714,024

(22) Filed: May 15, 2015

Related U.S. Application Data

(60) Provisional application No. 61/994,081, filed on May 15, 2014.

(51) Int. Cl.
*A61H 1/00* (2006.01)
*A61H 23/00* (2006.01)
(Continued)

(52) U.S. Cl.
CPC .............. *A61B 5/00* (2013.01); *A43B 3/0005* (2013.01); *A43B 3/30* (2013.01); *A61B 5/02* (2013.01);
(Continued)

(58) Field of Classification Search
CPC .... A61B 5/00; A61B 5/02; A61B 5/03; A61H 23/00; A61H 1/008; A61H 2201/0103;
(Continued)

(56) References Cited

U.S. PATENT DOCUMENTS

| 4,736,312 A | * | 4/1988 | Dassler | A43B 3/0005 235/105 |
| 5,396,896 A | * | 3/1995 | Tumey | A61H 9/0078 128/925 |

(Continued)

OTHER PUBLICATIONS

Patent Cooperation Treaty, International Search Report for PCT/US2016/050443, dated Nov. 29, 2016, pp. 1-2.
(Continued)

*Primary Examiner* — Tu A Vo
(74) *Attorney, Agent, or Firm* — Pillsbury Winthrop Shaw Pittman LLP

(57) ABSTRACT

Described herein are customized, intelligent outerwear created through additive manufacturing and integrated with a plurality of sensors, actuators and other electronics to monitor user activity and provide various diagnostic and therapeutic capabilities. The outerwear is additively manufactured using a three-dimensional ("3D") printer to provide for dynamic configurations of the sensors, actuators and other electronics depending on the specific needs of an individual. In addition to sensors for tracking motion, resistance, temperature and temporal features, the actuators may include piezoelectric components and microfluidic components to provide for therapeutic treatments, medical treatments and accident avoidance features. The combination of sensors and other electronics may also provide applications for monitoring overall health and growth.

22 Claims, 22 Drawing Sheets

(51) Int. Cl.
*A61B 5/00* (2006.01)
*B33Y 50/00* (2015.01)
*A43B 3/00* (2006.01)
*A43B 3/30* (2006.01)
*A61B 5/03* (2006.01)
*A61B 5/02* (2006.01)
*B29C 64/393* (2017.01)

(52) U.S. Cl.
CPC .............. *A61B 5/03* (2013.01); *A61H 1/008* (2013.01); *A61H 23/00* (2013.01); *B29C 64/393* (2017.08); *A61H 2201/0103* (2013.01); *A61H 2201/0207* (2013.01); *A61H 2201/1238* (2013.01); *A61H 2201/1409* (2013.01); *A61H 2201/165* (2013.01); *A61H 2201/1642* (2013.01); *A61H 2201/5061* (2013.01); *B33Y 50/00* (2014.12)

(58) Field of Classification Search
CPC .......... A61H 2201/0207; A61H 1/0266; A61H 2201/164; A61H 2203/0406; A61H 2205/12; A43B 3/30; A43B 3/0005; B33Y 50/00
See application file for complete search history.

(56) References Cited

U.S. PATENT DOCUMENTS

| | | | | |
|---|---|---|---|---|
| 5,443,440 A * | 8/1995 | Tumey | ................ | A61H 9/0078 128/DIG. 20 |
| 5,813,142 A * | 9/1998 | Demon | ................ | A43B 3/0005 36/28 |
| 5,875,571 A * | 3/1999 | Huang | ................ | A43B 3/00 36/132 |
| 5,914,659 A * | 6/1999 | Herman | ................ | A43D 1/027 340/573.1 |
| 6,195,921 B1 * | 3/2001 | Truong | ................ | A43B 3/00 340/573.1 |
| 6,836,744 B1 * | 12/2004 | Asphahani | ................ | A43D 1/02 377/24.2 |
| 6,944,327 B1 | 9/2005 | Soatto | | |
| 7,426,873 B1 * | 9/2008 | Kholwadwala | ........... | A43B 3/00 73/777 |
| 7,911,339 B2 * | 3/2011 | Vock | ................ | A43B 1/0036 340/540 |
| 9,201,413 B2 | 12/2015 | Hanft | | |
| 9,675,135 B2 | 6/2017 | Truitt et al. | | |
| 2002/0184790 A1 * | 12/2002 | Davis | ................ | A43B 3/26 36/1 |
| 2003/0009308 A1 * | 1/2003 | Kirtley | ................ | A61B 5/1038 702/141 |
| 2003/0184441 A1 * | 10/2003 | Nanayakkara | ........... | A61H 3/061 340/573.1 |
| 2003/0236588 A1 | 12/2003 | Jang et al. | | |
| 2007/0011173 A1 * | 1/2007 | Agostino | ................ | A43D 1/02 |
| 2007/0203435 A1 * | 8/2007 | Novak | ................ | A61B 5/1038 601/70 |
| 2008/0021531 A1 * | 1/2008 | Kane | ................ | A61F 7/02 607/111 |
| 2008/0066343 A1 * | 3/2008 | Sanabria-Hernandez | | A43B 3/0005 36/43 |
| 2008/0083416 A1 * | 4/2008 | Xia | ................ | A43B 7/142 132/200 |
| 2008/0097263 A1 * | 4/2008 | Grigoriev | ................ | A43B 7/00 601/151 |
| 2008/0167580 A1 * | 7/2008 | Avni | ................ | A43B 3/0005 600/587 |
| 2009/0005834 A1 * | 1/2009 | Weintraub | ......... | A61H 23/0263 607/48 |
| 2009/0007458 A1 * | 1/2009 | Seiler | ................ | A43B 3/00 36/136 |
| 2009/0038182 A1 * | 2/2009 | Lans | ................ | A43B 3/0005 36/136 |
| 2009/0051683 A1 * | 2/2009 | Goonetilleke | ......... | A43D 1/025 345/419 |
| 2009/0069865 A1 * | 3/2009 | Lasko | ................ | A61N 1/36003 607/49 |
| 2009/0126225 A1 * | 5/2009 | Jarvis | ................ | A43B 13/41 36/29 |
| 2010/0004566 A1 * | 1/2010 | Son | ................ | A43B 3/0005 600/592 |
| 2010/0010398 A1 * | 1/2010 | Mayer | ................ | A61H 23/02 601/27 |
| 2010/0063779 A1 * | 3/2010 | Schrock | ................ | A43B 3/00 702/188 |
| 2010/0094184 A1 * | 4/2010 | Wong | ................ | A43B 13/203 601/149 |
| 2010/0258358 A1 * | 10/2010 | Wiest | ................ | A43B 1/0054 177/245 |
| 2011/0040220 A1 * | 2/2011 | Holgreen | ................ | A61H 9/0078 601/148 |
| 2011/0054359 A1 * | 3/2011 | Sazonov | ................ | A43B 3/0005 600/595 |
| 2011/0153261 A1 * | 6/2011 | Jang | ................ | A43B 3/0005 702/141 |
| 2011/0251520 A1 * | 10/2011 | Shieh | ................ | A43B 3/0005 600/587 |
| 2012/0117822 A1 | 5/2012 | Jarvis | | |
| 2012/0166091 A1 * | 6/2012 | Kim | ................ | A61B 5/1038 702/19 |
| 2012/0186101 A1 * | 7/2012 | Sanchez | ............... | A43B 3/0005 36/44 |
| 2012/0311885 A1 * | 12/2012 | Moreshead | ............ | H05B 3/347 36/2.6 |
| 2013/0041298 A1 * | 2/2013 | Mayer | ................ | A61H 23/02 601/29 |
| 2013/0211281 A1 * | 8/2013 | Ross | ................ | A61B 5/01 600/549 |
| 2013/0211290 A1 * | 8/2013 | Lee | ................ | A43B 3/0005 600/592 |
| 2013/0346021 A1 * | 12/2013 | Stevens | ................ | G01C 22/006 702/160 |
| 2014/0070445 A1 | 3/2014 | Mayer | | |
| 2014/0137965 A1 | 5/2014 | Truitt et al. | | |
| 2014/0149072 A1 * | 5/2014 | Rutschmann | ........... | A43D 1/022 702/167 |
| 2014/0182170 A1 * | 7/2014 | Wawrousek | ............ | A43B 7/14 36/103 |
| 2014/0200834 A1 * | 7/2014 | Ross | ................ | A43B 3/0005 702/41 |
| 2014/0202042 A1 * | 7/2014 | Berend | ................ | A43B 13/141 36/25 R |
| 2014/0250723 A1 * | 9/2014 | Kohatsu | ................ | A43B 3/26 36/88 |
| 2014/0259785 A1 * | 9/2014 | Lester | ................ | A43B 13/026 36/102 |
| 2014/0259786 A1 * | 9/2014 | Heard | ................ | A43B 13/14 36/103 |
| 2014/0260677 A1 * | 9/2014 | Dojan | ................ | G01L 1/2206 73/862.045 |
| 2014/0277631 A1 * | 9/2014 | Rice | ................ | G01L 1/2206 700/91 |
| 2014/0277658 A1 | 9/2014 | Hanft | | |
| 2014/0291886 A1 * | 10/2014 | Mark | ................ | B29C 64/118 264/163 |
| 2014/0374933 A1 | 12/2014 | Flitsch et al. | | |
| 2014/0379119 A1 | 12/2014 | Sciacchitano et al. | | |
| 2015/0035200 A1 * | 2/2015 | Karpas | ................ | B29C 33/52 264/255 |
| 2015/0064047 A1 | 3/2015 | Hyde et al. | | |
| 2015/0088301 A1 | 3/2015 | Erdim et al. | | |
| 2015/0096426 A1 | 4/2015 | Culver et al. | | |
| 2015/0165690 A1 * | 6/2015 | Tow | ................ | B33Y 80/00 700/119 |
| 2015/0182316 A1 | 7/2015 | Morales et al. | | |
| 2015/0197060 A1 | 7/2015 | Carr et al. | | |
| 2015/0217520 A1 | 8/2015 | Karpas et al. | | |

(56) References Cited

U.S. PATENT DOCUMENTS

| | | | |
|---|---|---|---|
| 2015/0246496 A1 | 9/2015 | Jones et al. | |
| 2015/0321418 A1* | 11/2015 | Sterman | B29C 41/36 |
| | | | 264/40.7 |
| 2015/0321434 A1* | 11/2015 | Sterman | B29C 37/0078 |
| | | | 264/255 |
| 2016/0072986 A1 | 3/2016 | Jones | |
| 2016/0349738 A1 | 12/2016 | Sisk | |
| 2016/0374431 A1 | 12/2016 | Tow | |
| 2017/0055880 A1* | 3/2017 | Agrawal | A61B 5/1038 |
| 2017/0068774 A1 | 3/2017 | Cluckers et al. | |

OTHER PUBLICATIONS

Huang et al., Highly Flexible and Conductive Printed Graphene for Wireless Wearable Communications Applications, Scientific Reports, Dec. 17, 2015, pp. 1-7.

Zhang et al., Fabrication of highly conductive graphene flexible circuits by 3D printing, Synthetic Metals, Jul. 2016, pp. 79-86, vol. 217.

Carey et al., Fully inkjet-printed two-dimensional material fieldeffect heterojunctions for wearable and textile electronics, Oct. 31, 2017, pp. 1-11.

Halterman, TE, How a Ukrainian Mathematician Can Make Your 3D Printed Models Look Better, accessed online at https://3dprint.com/62325/3d-printing-voronoi-models/, May 3, 2015, pp. 1-3.

Stevenson, Kerry, Voronoization, accessed online at http://www.fabbaloo.com/blog/2013/5/21/voronoization.html, May 21, 2013, pp. 1-3.

Peck, Marshall, Make 3D Printable Voronoi Patterns With Autodesk® Meshmixer, accessed online at http://www.instructables.com/id/Make-Voronoi-Pallem-with-Autodesk-Meshmixer/, Apr. 30, 2015, pp. 1-2.

McCue, T J, How to Make Voronoi Pattern with 3D Printer, accessed online at hllps://www.lifewire.comvoronoi-pattern-with-3d-printer-2218, May 3, 2018, pp. 1-3.

* cited by examiner

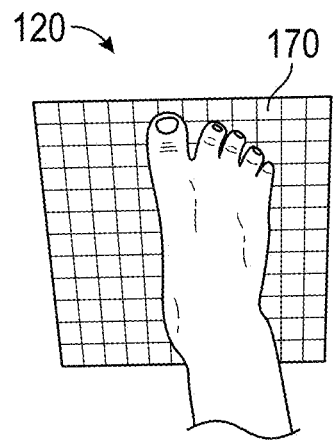
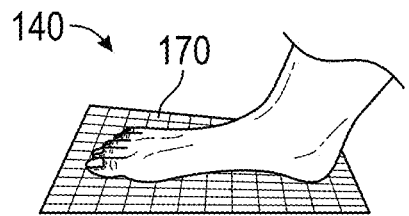
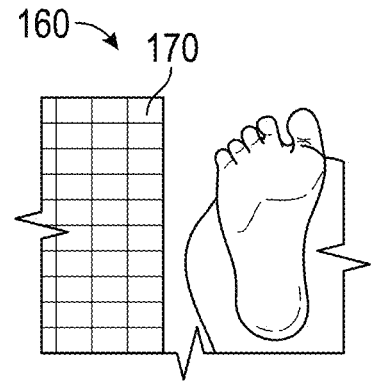
FIG. 1A　　　FIG. 1B　　　FIG. 1C
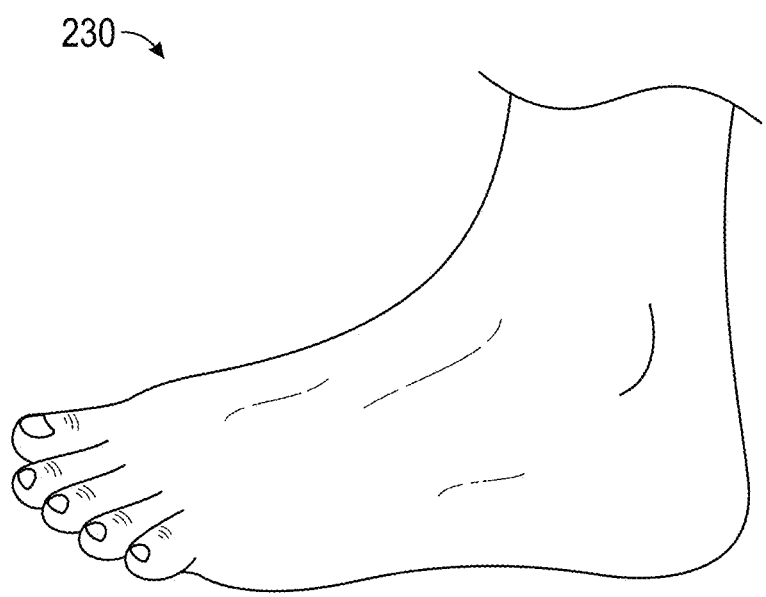
FIG. 2

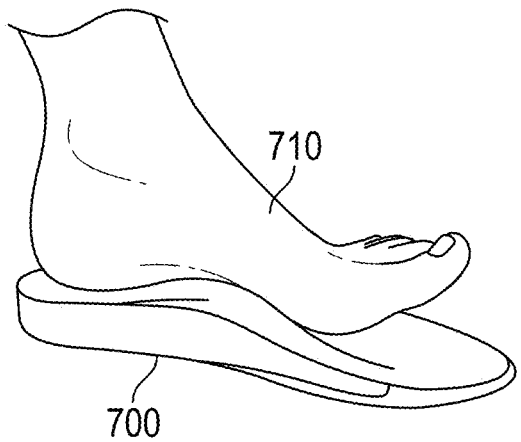

FIG. 7A

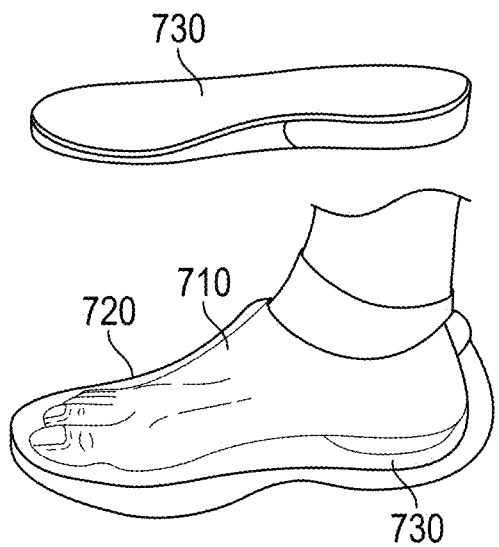

FIG. 7B

Orthotic Insoles (Customizable)

[Parameters]

Heal Width Width of the Heel of Your Foot (in Millimeters)

[ 60 ]

Foot Width Width of Your Foot Where Your Arch Ends (in Millimeters)

[ 72 ]

Beginning of Arch Distance from the Back of Your Heel to the Start of Your Arch (in Millimeters)

[ 50 ]

End of Arch Distance from the Back of Your Heel to the End of Your Arch (in Millimeters)

[ 131 ]

Arch Height Height of Your Arch from the Ground, with no Weight on Your Foot (in Millimeters)

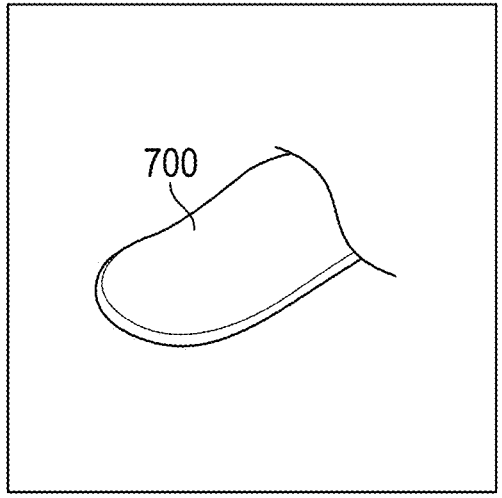

INTELLIGENT, ADDITIVELY-MANUFACTURED OUTERWEAR AND METHODS OF MANUFACTURING THEREOF

BACKGROUND

Field of the Invention

Provided herein is customized, intelligent outerwear created using additive manufacturing, and more specifically additively-manufactured outerwear configured with sensors, actuators and other electronics to provide diagnostic and therapeutic capabilities.

Related Art

In the shoe industry, a typical shoe is designed for the mass consumer and provides little or no customization. A consumer may spend years purchasing different brands or styles of shoes in search of the best fit. Even if a consumer finds one brand that fits comfortably for a particular style (such as a dress shoe), that brand may not provide a similar fitting shoe in a different style (such as a sneaker). Thus, consumers must go through continuous trial and error to find shoes which are comfortable and appeal to their personal style. This process is often unsuccessful, with consumers sacrificing style for comfort, or vice-versa.

For those who are interested in customization, a bespoke cobbler can build a customized shoe around a last of the customer's feet. However, this process may cost in excess of $1000 and take several months. For consumers with medical or physical issues, such as physical disabilities or deformities, customized shoes, or other accessories must be obtained from a health care provider or medical device manufacturer—often at great cost—and even then the shoe is only designed to generally alleviate a disability without being customized for the particular user.

Three-dimensional ("3D") printing, also known as additive manufacturing, may provide a solution to the difficulties of customizing footwear. The cost of 3D printing is significantly less than the traditional manufacturing process and can also be completed in very little time. However, the current 3D printing technologies use materials which are not comfortable, durable or stylish. More importantly, 3D printing has no adequate mechanism for creating a shoe based on a specific user's foot.

Therefore, there is a need for footwear and even general outerwear which can be designed and customized for an individual consumer.

SUMMARY

Embodiments described herein provide for customized, intelligent outerwear created through additive manufacturing and integrated with a plurality of sensors, actuators and other electronics to monitor user activity and provide various diagnostic and therapeutic capabilities. The outerwear is additively manufactured using a three-dimensional ("3D") printer to provide for dynamic configurations of the sensors, actuators and other electronics depending on the specific needs of an individual. In addition to sensors for tracking motion, resistance, temperature and temporal features, the actuators may include piezoelectric components and microfluidic components to provide for therapeutic treatments, medical treatments and accident avoidance features. The combination of sensors and other electronics may also provide applications for monitoring overall health and growth.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which:

FIGS. 1A-1C illustrate images of a foot utilized for generating a point cloud map to create a three-dimensional ("3D") model, according to an embodiment of the invention;

FIG. 2 is an illustration of a 3D model of a foot, according to an embodiment of the invention;

FIGS. 7A-7C illustrate an insole which may be utilized inside the 3D printed shoe to fit a user's foot, according to one embodiment;

FIG. 18 is a block diagram illustrating an example wired or wireless processor enabled device that may be used in connection with various embodiments described herein.

DETAILED DESCRIPTION

Figure 3A:
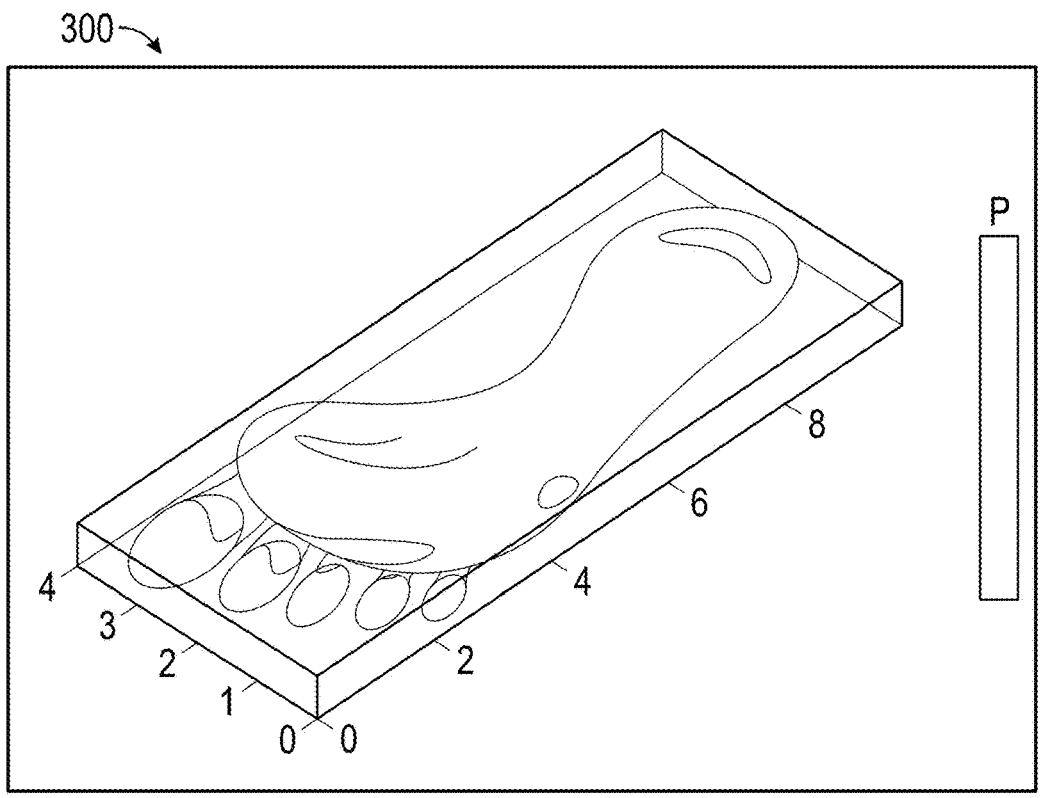
FIGS. 3A and 3B are illustrations of a pressure map of a foot, according to an embodiment of the invention.

Embodiments described herein provide for systems and methods of creating a three-dimensional ("3D") model of a body part, such as a foot, and using the 3D model to develop a customized, additive-manufactured shoe. A user may capture images of the foot, which are then transformed into a point cloud map to create a 3D model of the user's foot. The 3D model may be analyzed, along with information on the user's movement, activities and physical history, to determine the properties and features for a customized shoe that is designed specifically for the user's foot. The customized shoe is then designed for additive manufacturing through the use of specific materials, patterns, shapes to provide a customized shoe which is perfectly fit to the user's foot. The customized shoe may also be designed with different exterior styles and integrated with one or more sensors or other electronics to capture user data, provide unique therapeutic or medical treatments, and intelligently predict health or growth issues. The same principles may be applied to other types of outerwear, such as headwear, clothing, gloves, etc.

The ability to generate a 3D model of a body part such as a foot from a few images provides a simple and effective method to obtain a 3D-printed shoe which is perfectly customized to a user's foot. In addition to the overall 3D shape of the shoe matching the shape of the 3D model of the foot, the shoe itself may be manufactured from specific materials, specific patterns and shapes that provide comfort, durability, flexibility and dynamic responses to their environment.

Although the embodiments described herein below refer to a foot and a shoe configured for the foot, the same principles can apply to any garment, fashion accessory or item of clothing/outerwear that can be form fitted from a 3D representation of the item to be covered. Examples include, but are not limited to, e.g. gloves, shoes, sport shoes, ski boots, motorcycle helmets, cycling helmets, eye glasses, sun glasses, shirts, trousers, shorts, skirts, dresses, jackets, suits, coats, etc.

I. Creating a Three-Dimensional Model

In one embodiment, in order to create a three-dimensional ("3D") model of a body part, images 120, 140, 160 are captured of the body part on a grid 170 from a few different angles, as illustrated in FIGS. 1A-1C, respectively. The images may be obtained using an image capture device such as a digital camera, or a mobile device with an integrated image sensor, such as a smartphone, tablet, etc. Additionally, webcams, KINECT sensors, game consoles and even scanners may be used. The images may be and/or include still images, video images, and/or other images (e.g., a collection of images gathered at 30 frames/second (this frame rate is not intended to be limiting) may be parsed into separate strings of images).

These images are stitched together using algorithms that create a 3D representation of each foot from the images. This generates a point cloud map from the image data.

Next, to generate a 3D model, or 3D foot last, from the point cloud data, the point cloud image is taken and snapped into a dynamic shaping algorithm that matches foot dimensions. Point cloud approximations of the appendages are generated and provide 3D foot last that represents the original dimensions of each foot. This data can be imported into 3D CAD packages for manipulation. Point cloud data points are superimposed on a pre-existing digital foot model and dynamic adjustments are made to create an individual custom digital last. An illustration of one embodiment of the 3D model 230 is shown in FIG. 2.

Figure 3B:
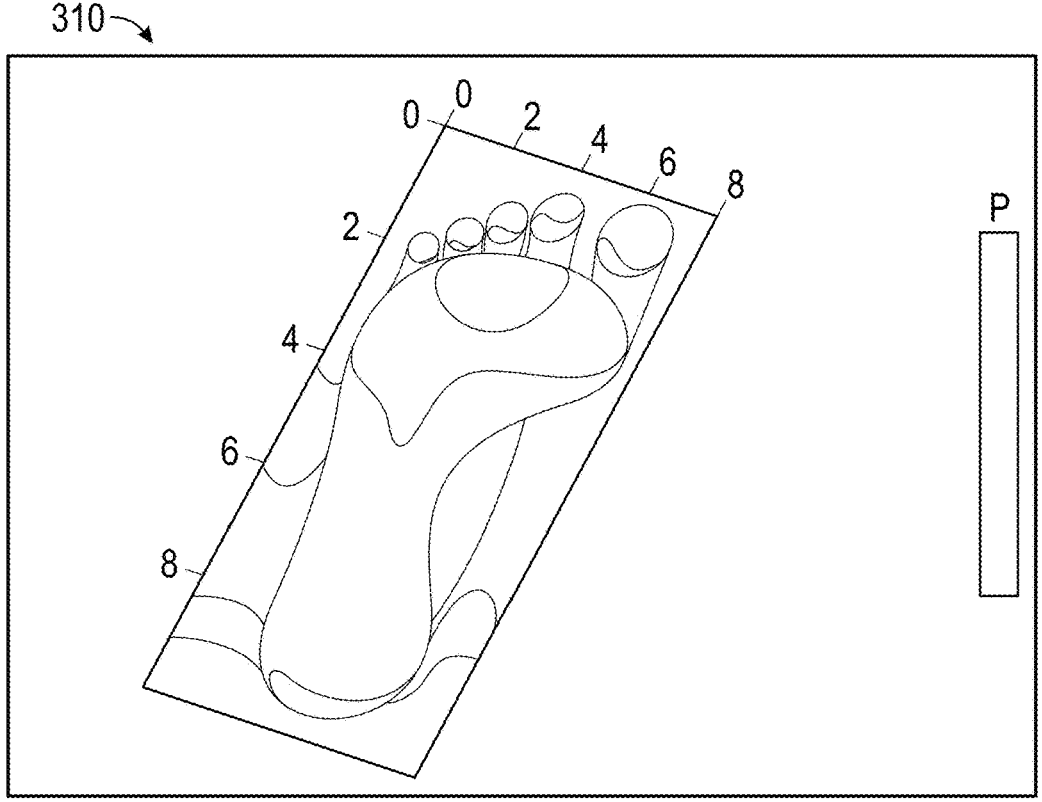

In addition to determining the shape of the foot, additional measurements may be taken to determine the pressure points on the foot, as shown in the pressure maps 300, 310 in FIGS. 3A and 3B, respectively. The areas of the foot which experience greater pressure are shown in lighter shading on the foot, while areas with less pressure are shown in darker shading. The maps indicate where each user's feet exert pressure, which is helpful when designing a custom shoe, as the shoe can be configured to relieve pressure on the greatest pressure points. The pressure maps are generated based on the unique shape of each foot being mapped as applied to sets of rules for where pressure is applied on various parts of the foot.

II. Designing a Three-Dimensional Shoe

Once the 3D model has been generated, a custom fit shoe is then generated by snapping a pre-designed external shell to the point cloud data generated from the 3D model of each foot. Then, form and function fitting slicing algorithms are applied that adjust the model to provide user known biomechanics and custom preferences for fitness. These biomechanics may be entered manually by the user or obtained through collection of movement data from wearable devices.

In one embodiment, a shoe is designed in at least 3 components that can be manufactured from a FDM printer in "flat" pieces and assembled together. Each component must be designed to a 'standard foot shape.' The design must be grouped so that the re-sizing can be done together, as well as separate files to allow for the specific sizing needed on each component and for manufacturing in different materials.

Figure 4:
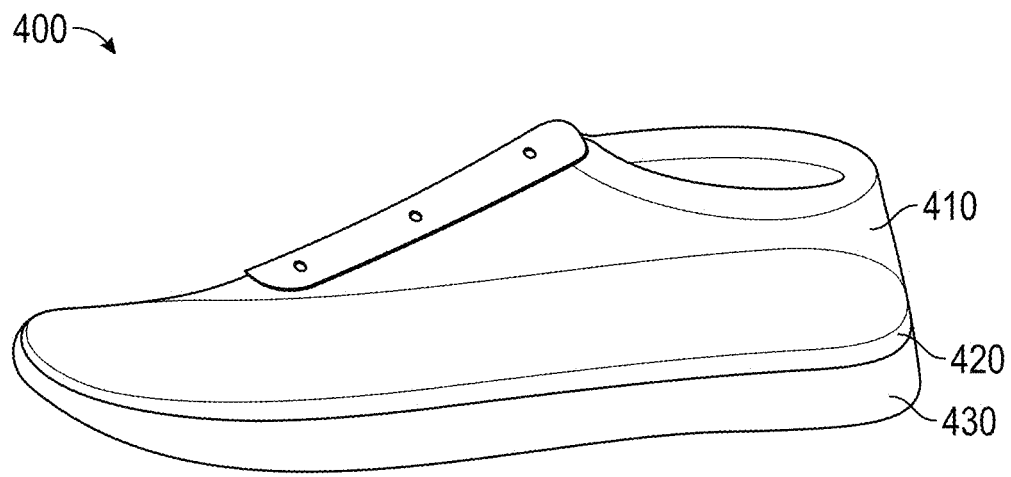
FIG. 4 is an illustration of three shoe components utilized for designing a shoe, according to one embodiment.

FIG. 4 illustrates a general concept of three shoe components required for one embodiment of a 3D printed shoe 400, including the shoe upper 410, insole/midsole 420 and outsole 430. These specific components are further defined immediately below.

Shoe Upper—the design and visual element of the shoe. This will be a parametric design and determined in combination from the user design and foot measurements/requirements. This is connected to the midsole of the shoe through an interlocking tab design.

Midsole—the internal component of the shoe. A base 'foot midsole block' is required that will then be modified to fit the user based on their calculated foot measurements and footwear functional requirements. This is a proprietary algorithm. The midsole will be connected to both the Shoe Upper and the Outsole.

Outsole—the base of the shoe. It will require the Feetz logo, a tread pattern, and an interlocking tab holes to connect to the Midsole component.

The completed 3D generated model must then be prepared for 3D printing. This is done by "slicing" the model into many layers, and is achieved through the creation of a comfort algorithm of form and function. Slicing can be achieved by any of the following methods, although these should not be considered limiting:

A. Basic approach—driven off commercial slicer models, e.g. rectilinear, concentric circles, triangles etc. All layers are treated the same throughout the entire 3D model.

B. Semi-custom approach—use a combination of pre-formed internals geometric shapes e.g. circle, triangle etc. and change the size, frequency and distribution to match the dynamics of the foot.

C. Parametric approach—create a parametrically driven mesh structure that is unique to every individual. E.g math based curvature orientated structures that can be further customized by e.g. based of the DNA of that individual.

D. User-driven shapes—allowing for complete customization e.g. heart shaped, dog bone shaped, or any structure that is designed by the individual which is packaged by our software to be the mesh.

E. Creating a complete shoe; e.g. different shoe sizes look the same. Automatically fits around the shell with deformities, and around toes.

F. Creates an automatic weight distribution for a pair of shoes:
  i. Same size outer shoe with different size feet
  ii. Customized based on user needs to be the same weight shoe or different weight shoe depending on the need.

Figure 5:
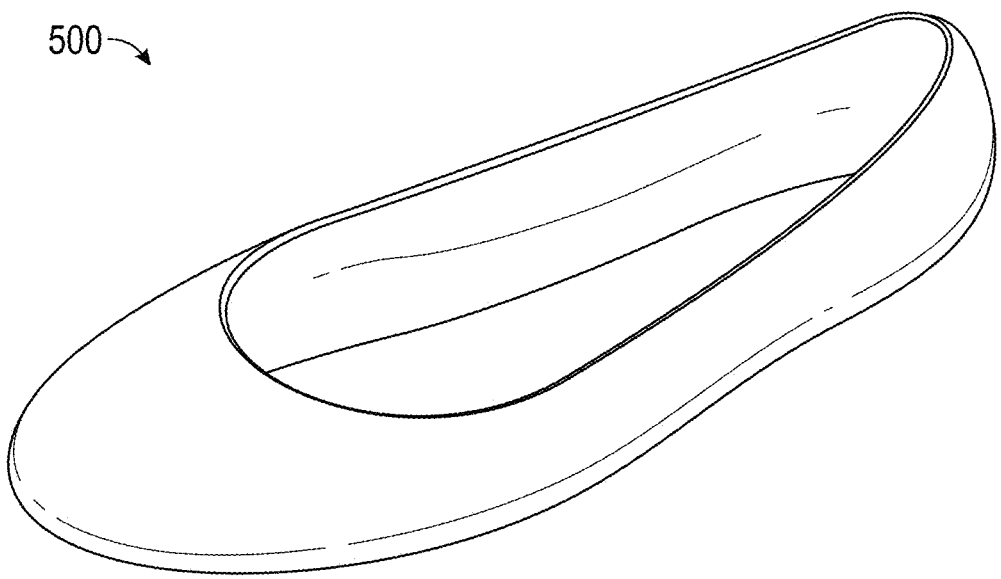
FIG. 5 is an illustration of a 3D printed shoe, according to one embodiment.
Figure 6A:
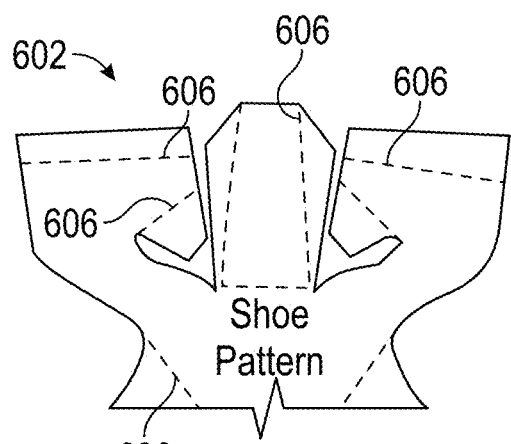
FIGS. 6A-6H are illustrations of materials, patterns and shapes used to create the 3D printed shoe, according to multiple embodiments.
Figure 6B:
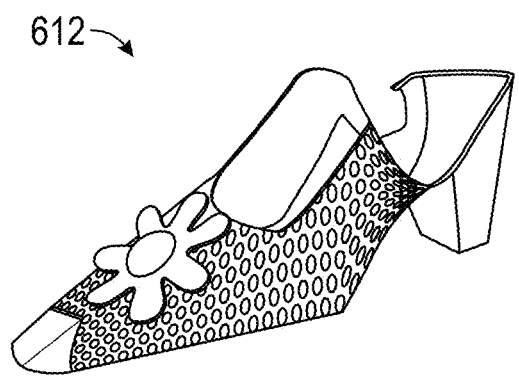
Figure 6C:
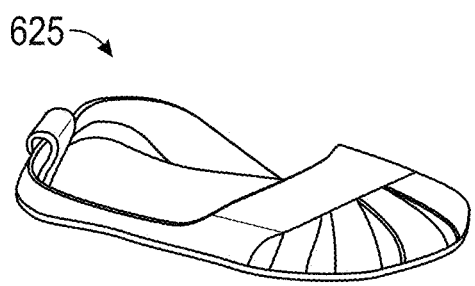
Figure 6D:
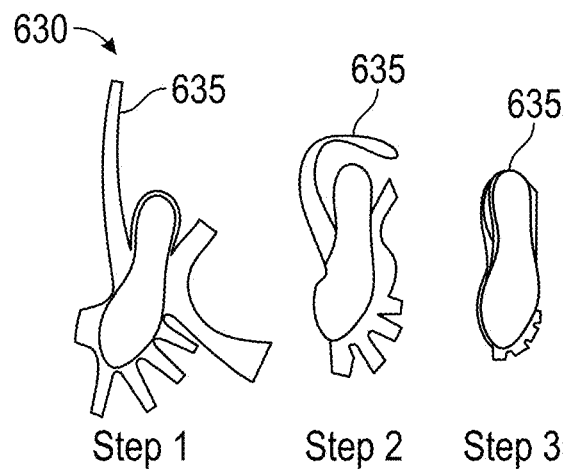
Figure 6E:
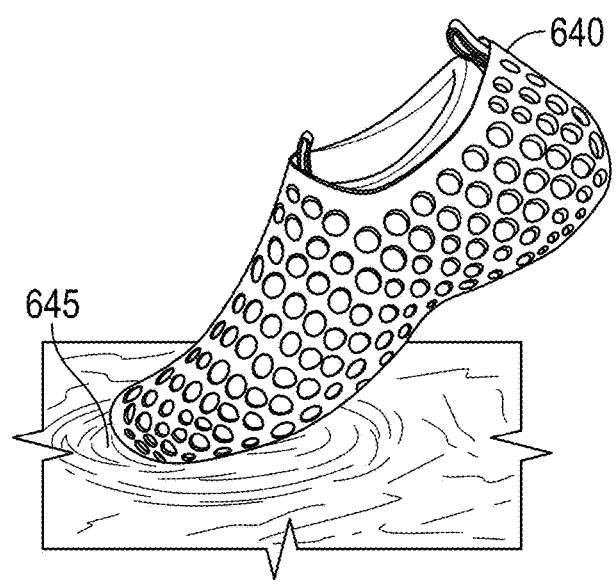
Figure 6F:
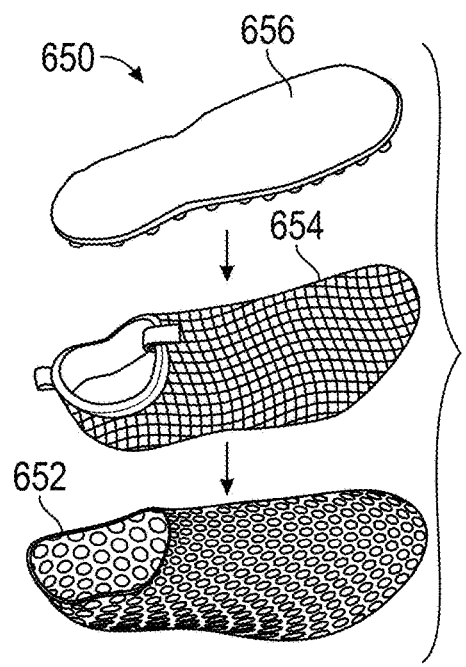

FIG. 5 illustrates a computer-graphic of a 3D-printed shoe 500 in accordance with one embodiment of the invention. This shoe is a single piece of material which does not require additional attachment steps. In addition, FIGS. 6A-6H illustrate several examples of separate components of a shoe which would be printed separately and attached to another component of the shoe, such as by folding, sleeves, interlocking tabs, etc. For example, FIG. 6A illustrates a template 602 for a pattern for making a shoe by folding along the dotted lines 606. FIGS. 6B and 6C illustrate examples of shoes 612 and 625, respectively. FIG. 6D illustrates a sequence of steps 630 for folding a shoe pattern 635 into a shoe such as shoe 625 of FIG. 6C. Similarly, FIG. 6F illustrates components 652, 654, 656 for producing a shoe 650. A shoe 640 stepping into puddle 645 is shown in FIG. 6E.

Figure 6G:
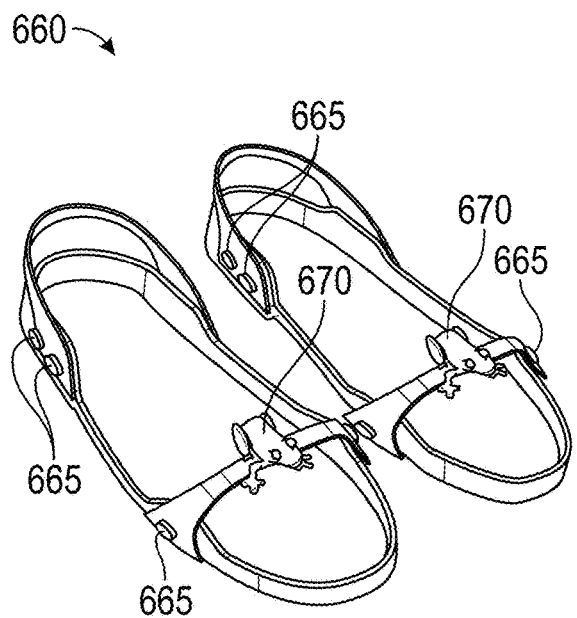
Figure 6H:
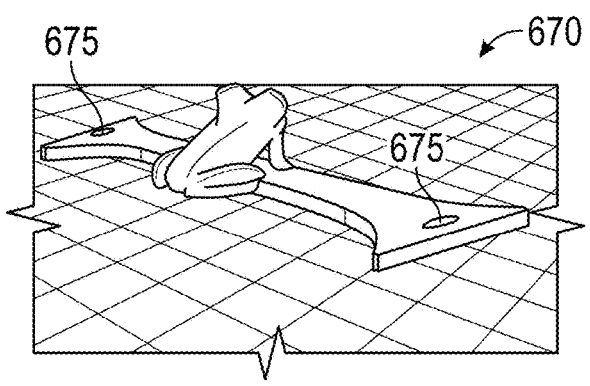

FIGS. 6G and 6H illustrate additional aspects of shoes 660 in accordance with some embodiments.

In one embodiment, the MidSole (for instance, the same as or similar to 420 in FIG. 4) is to be a design file for the left and the right foot that can be printed in a single component using an FDM 3D printer without the need for support material. This component is then attached to the other shoe components using an interlocking tab design. The material is a proprietary blend combining flexibility (rubber, polyurethanes) and durability (nylon, plastics). This will allow the piece to be customized to the user footwear requirements. Further components of the midsole are as follows:

MidSole Standard Base—a design base for a midsole as per FIG. 7A. It has registered points on the design file that can be attached to a customizable algorithm as in FIG. 7C for a custom fit to the user. FIGS. 7A-7C illustrate a midsole/insole 700 (for instance, the same as or similar to 420 in FIG. 4) that fits to a user's foot 710 and is inserted into a shoe 720 as a removable insert 730. In FIG. 7C, a graphical user interface (GUI) illustrates how an orthotic insole may be customized for a specific user.

Figure 8:
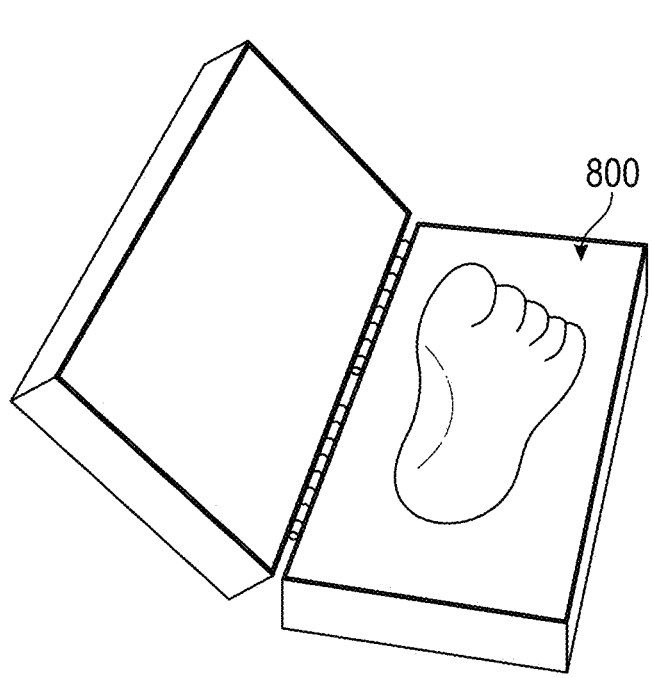
FIG. 8 is an illustration of a foam product which may be utilized to capture a person's specific foot shape, according to one embodiment.

MidSole Block Fill—a 'filled' design block that will be virtually fit to a user's foot based upon their virtual foot. See FIG. 8 for a visual. In this case the design "block" would be of a base midsole shape and design and not a cube. FIG. 8 is an example of foot foam 800 that is used to capture a person's specific foot shape 810. It is a visual for the Midsole criteria option (b) where foot virtually pressed into the midsole for a custom design shape.

MidSole Sections—in addition to the 2 options above, the midsole design will have 3 sections applied into the file with points of measurement where a unique algorithm of infill ratios and patterns will be applied to match the user functional requirements. See FIG. 12D for a visual example. In FIG. 12D, a FitFlop WobbleBoard technology allows for design tailored to a specific use case "exercise whilst you walk". This example is an illustration of the ability to design 'sections' in the midsole that can be customized to an individual user requirement.

Figure 9:
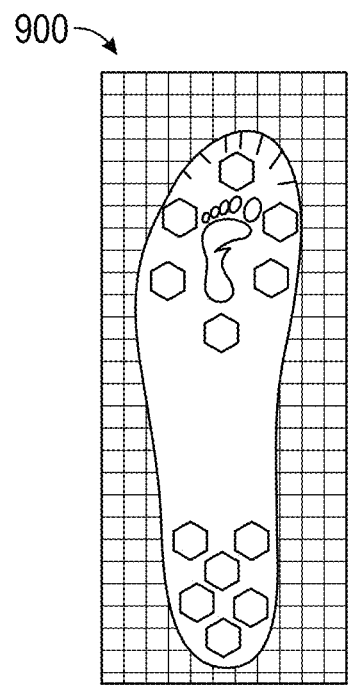
FIG. 9 is an illustration of a pattern on a sole of the 3D printed shoe, according to one embodiment.

The Outsole is to be a design file that can be printed in a single component using an FDM 3D printer without the need for support material. This component is then attached to the other shoe components using an interlocking tab design. The outer will require a tread pattern 900, and may also include a logo or branding, as shown in FIG. 9. Material is a proprietary blend combining flexibility (e.g., rubber, polyurethane) and durability (e.g., nylon, plastics). It will contain less flexibility than the other 2 components to provide foot support and durability in exposure to external surface contact.

Figure 10A:
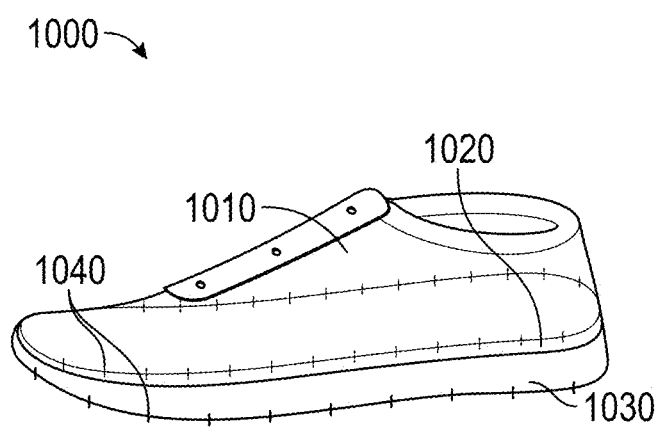
FIGS. 10A and 10B illustrate the use of shoe interlocking tabs, according to one embodiment.
Figure 10B:
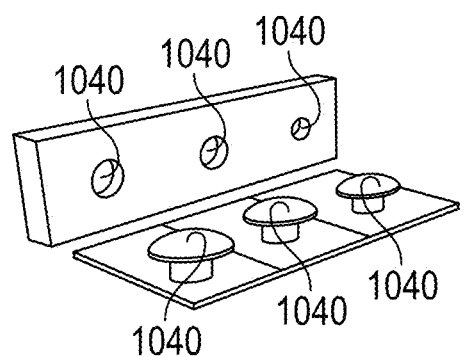

Another potential shoe component design is a set of interlocking tabs, as illustrated in FIG. 10A. The shoe components 1010, 1020, 1030 are to be combined together to form the shoe 1000 using a combination of footwear adhesives and a designed shoe interlocking element 1040 shown schematically in FIG. 10A. FIG. 10B specifically shows the design file of example interlocking tabs 1040. It is made using flexible materials, which allows the tab to be squeezed into the tab hole and then expanding to create a locking mechanism. The tab on the far left produced the strongest lock.

Examples show options for this locking mechanism suitable for different materials. FIG. 4 is suitable for flexible materials because it can be squeezed into the hole. Tabs are needed in the 3 components of the shoe to keep the pieces held together tightly.

The number of tabs will need to vary with the actual size dimensions, design will need to be flexible to allow for this to occur. For instance, a large size 17 shoe will have more tabs than a small size 4 shoe. Tab Locations/Directions on each component are to be determined.

Figure 11A:
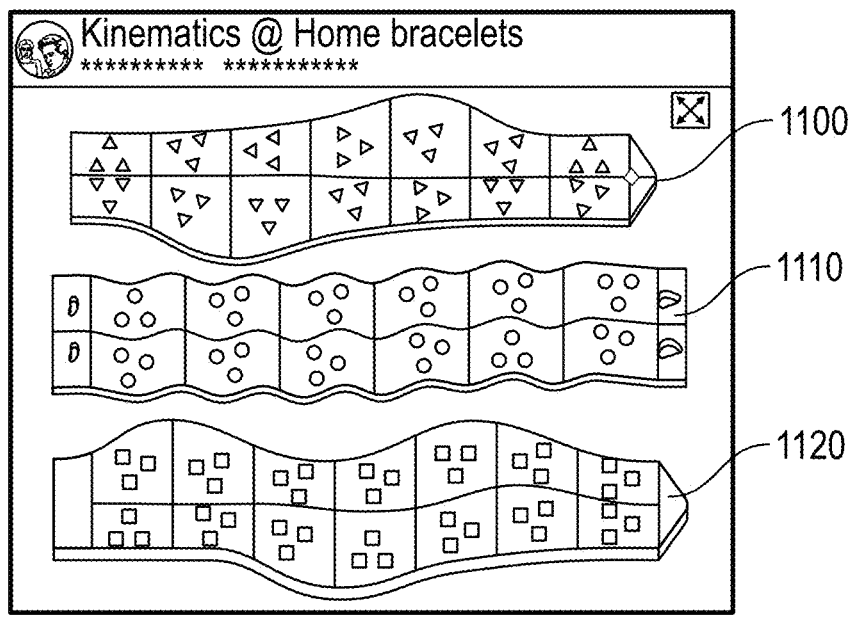
FIGS. 11A-11C illustrate a concept of a flexible, bendable joint used for 3D printing, according to one embodiment.
Figure 11B:
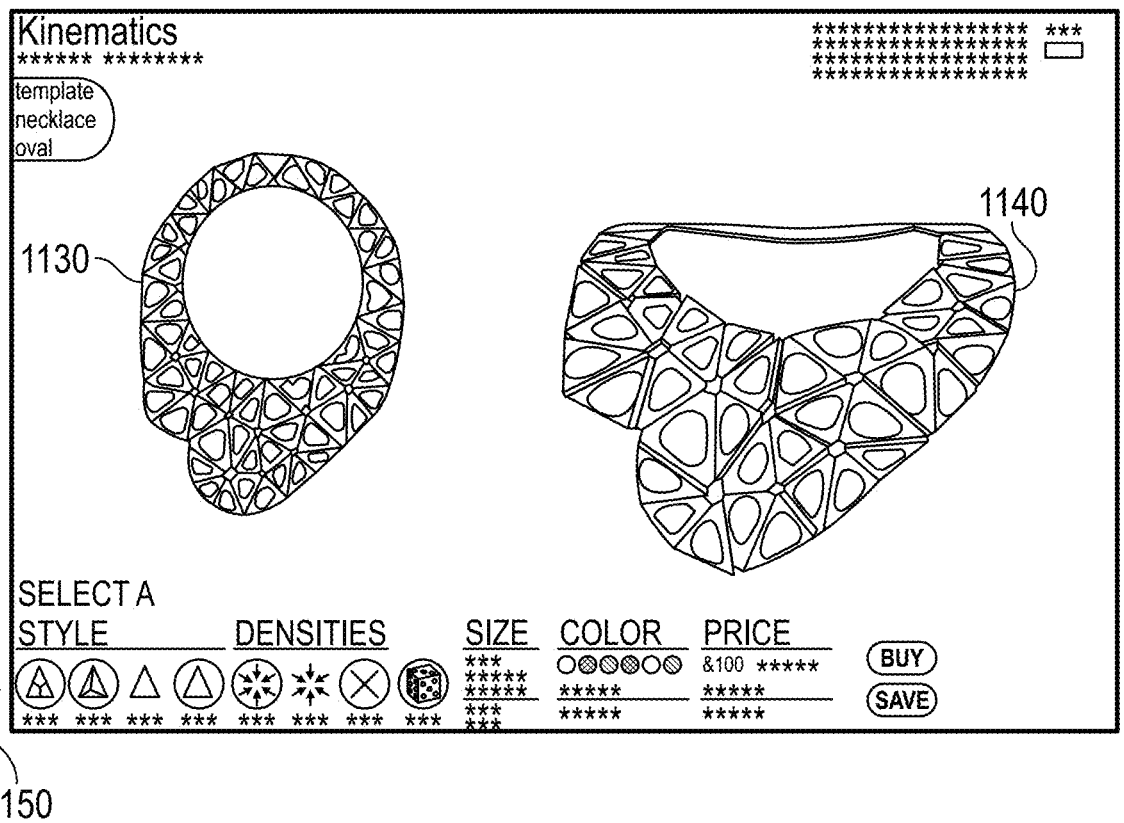
Figure 11C:
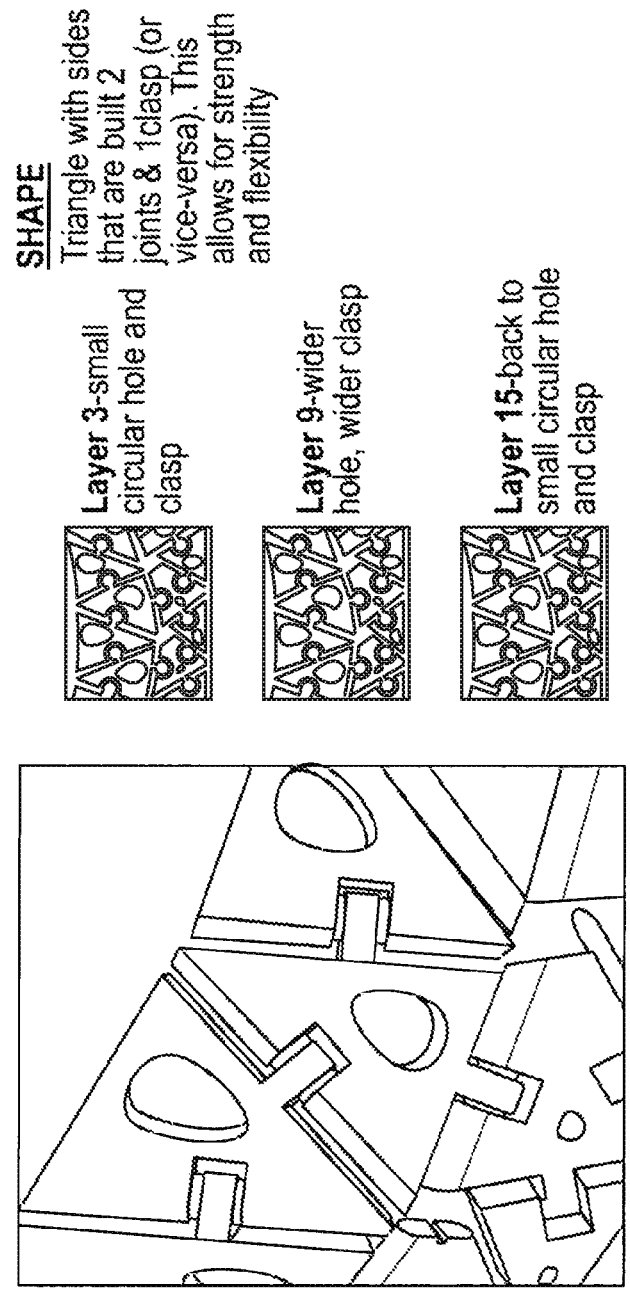

A further design consideration is the use of flexible bendable joints, as shown by the materials in FIGS. 11A and 11B. This is an example to a design method used to bring a flexible bendable joint to a 3D printed object that is made using an FDM printer in hard plastic material, and as mentioned above. FIG. 11A illustrates examples of three different flexible bendable joint designs 1100, 1110, 1120 with different patterns which may be created in some embodiments. FIG. 11B shows more detailed views 1130, 1140 of an example of a flexible bendable joint design embodiment. FIG. 11B also illustrates aspects of a user interface 1150 that enables a user to select various parameters associated with an outerwear design such as style, material density, size, and color. The flexible bendable joint design examples shown in FIGS. 11A and 11B are suitable for hard plastics where a joint can be created. A close-up view of the joint and the layer build approach is shown in FIG. 11C, which shows it as a ball bearing approach. In the illustrated embodiment, the ball bearing style design comprises interlocking triangles with sides that incorporate either 2 holes and 1 clasp or vice versa, thereby allowing for strength and flexibility.

Figure 12A:
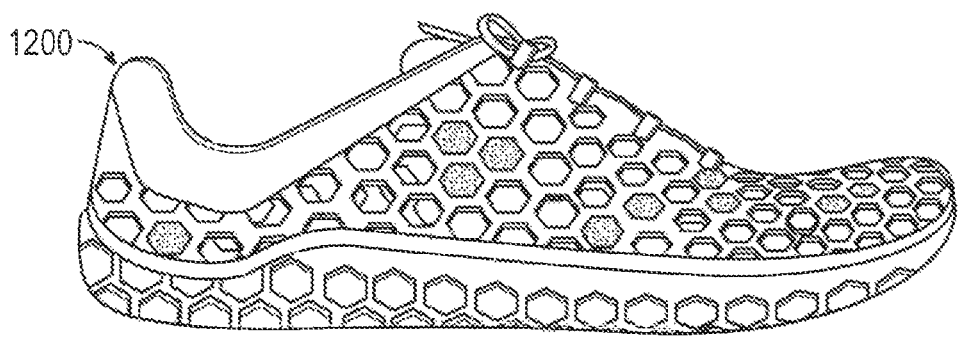
FIGS. 12A-12E illustrate additional shapes of a 3D printed shoe, as well as different properties of different portions of a 3D printed shoe, according to one embodiment.
Figure 12B:
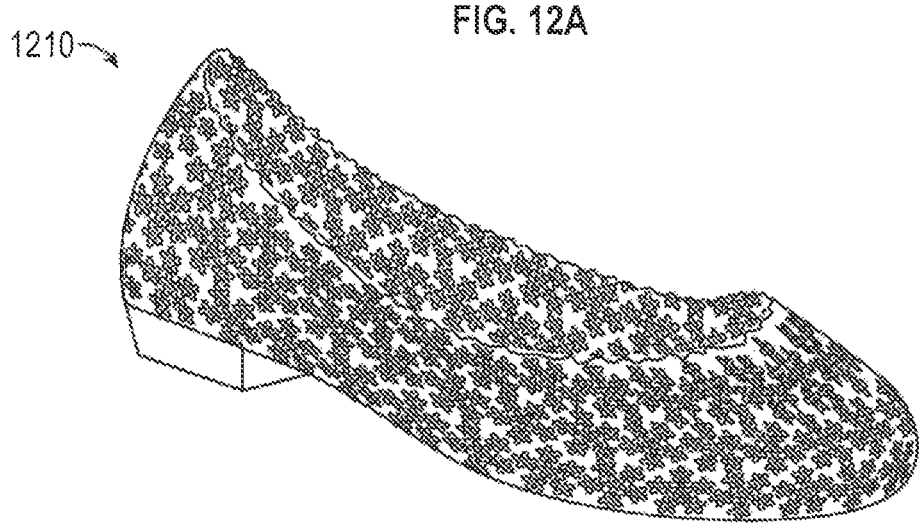
Figure 12C:
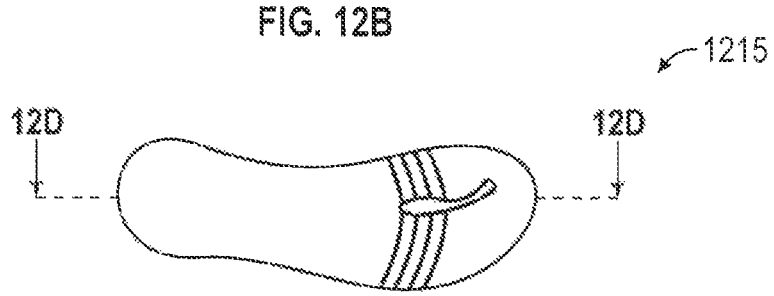
Figure 12D:
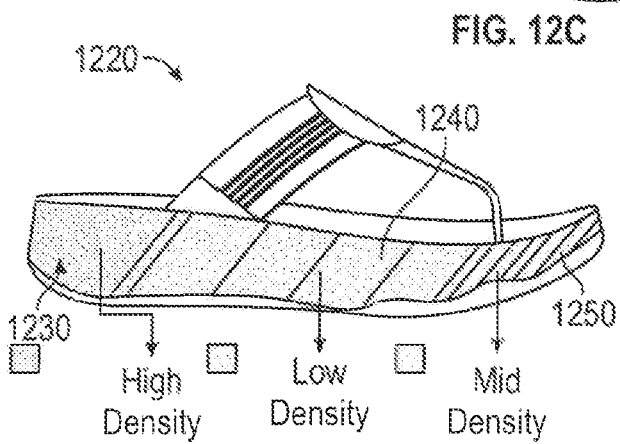
Figure 12E:
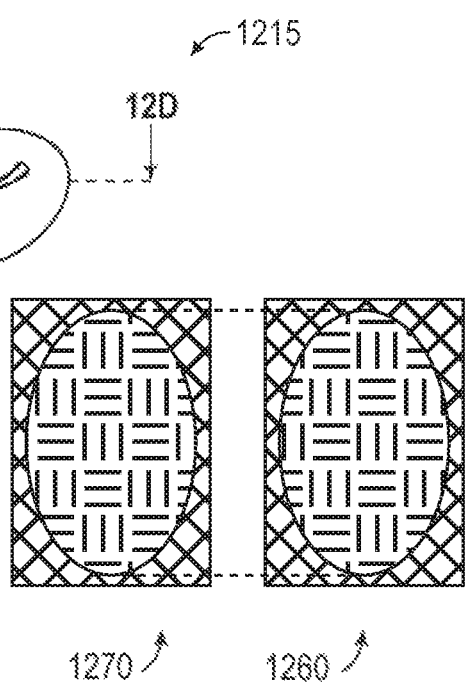

FIGS. 12A-12E illustrate additional design options for the shoe which demonstrate that the outer portion of the shoe may be designed in practically any known shape to provide for a unique style, color. FIG. 12A illustrates a shoe design 1200 according to some embodiments. FIG. 12B illustrates an alternative shoe design 1210 according to some embodiments. FIG. 12C illustrates a top view of a shoe design 1215 according to some embodiments. FIG. 12D illustrates a cross sectional view 1220 of an embodiment of the shoe design of FIG. 12C incorporating several types of materials according to some embodiments. In the illustrated design, the heel portion of the shoe is made from a high density material 1230, the middle portion is made from a low density material 1240, and the toe portion of the shoe is made from a medium or mid density material 1250. FIG. 12E schematically illustrates a detail of a slicer model incorporating an angular rotation between consecutive layers 1260 and 1270, for example 20 degrees, according to some embodiments.

Figure 13:
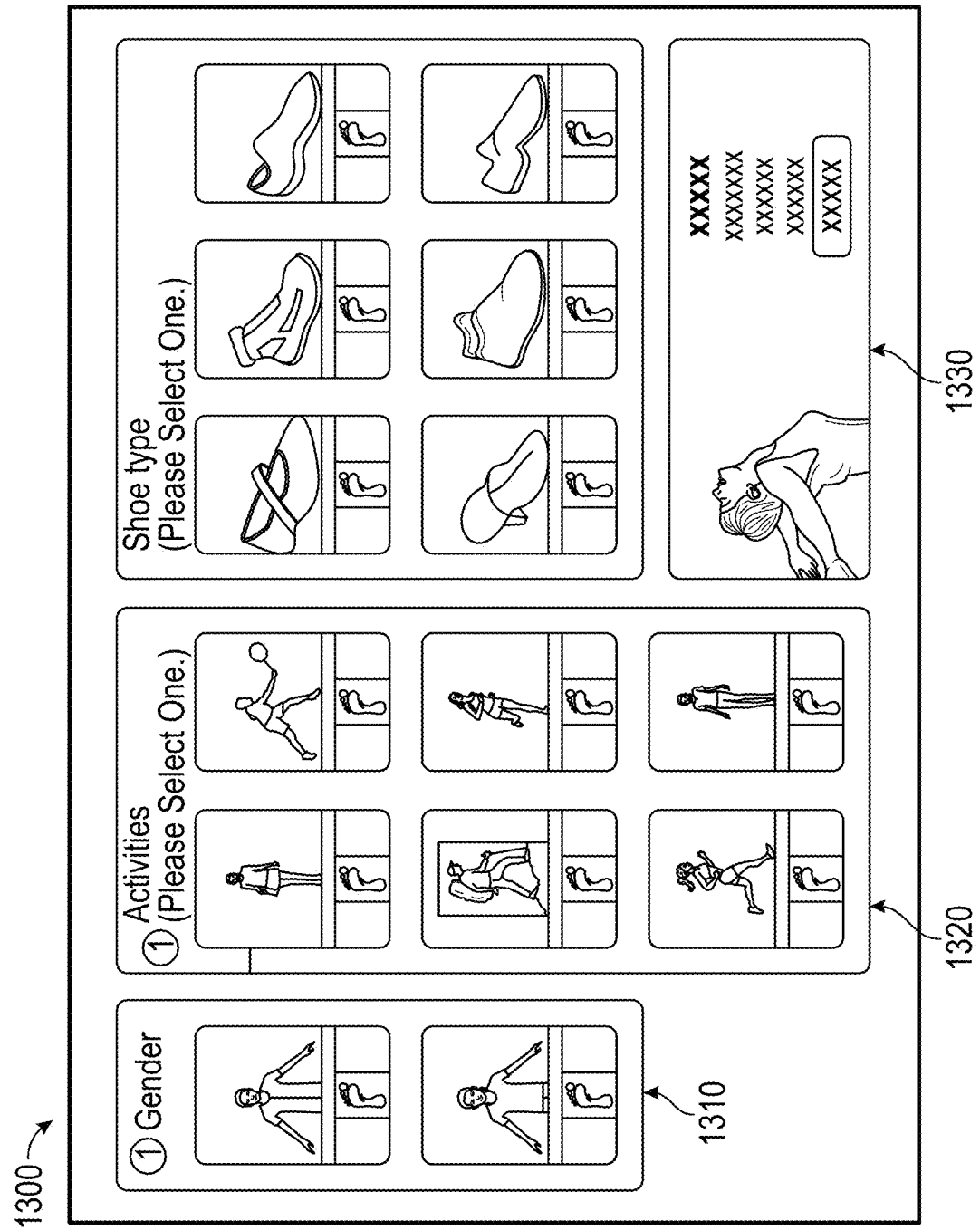
FIGS. 13 and 14 are illustrations of a graphical user interface presented to a user for customizing their shoe, according to one embodiment.
Figure 14:
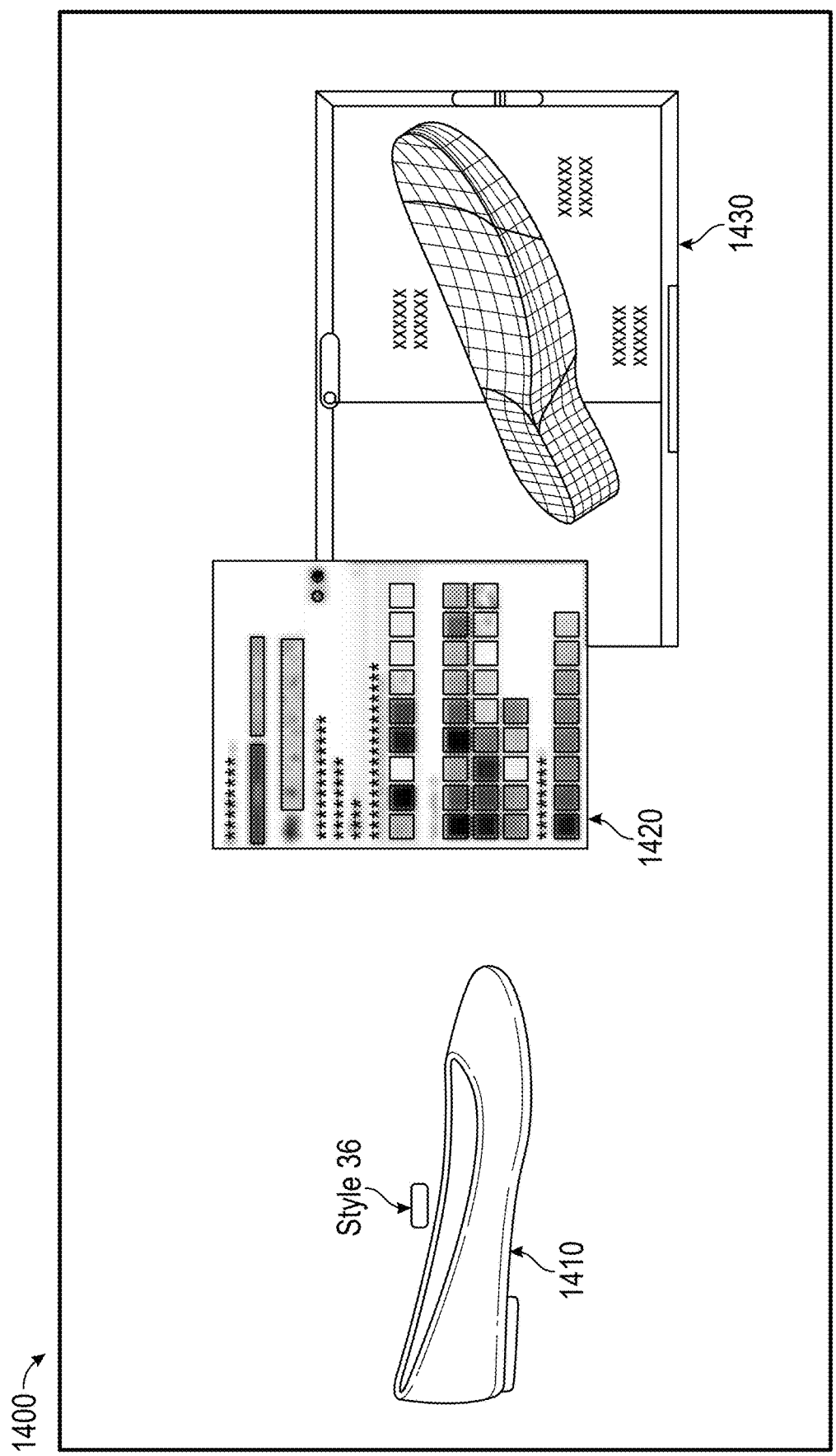

An example of a graphical user interface (GUI) where the user is able to select their activities and other aspects of the shoe is shown in FIGS. 13 and 14. FIG. 13 illustrates a GUI 1300 of a website including interactive elements 1310, 1320, and 1330 for obtaining a user's gender, activity, and shoe style, respectively, according to some embodiments. FIG. 14 illustrates further aspects of a GUI 1400, for example of a website including alternative or additional elements 1410, 1420, and 1430 for example for visually displaying information about shoe design options with user requirements such as style, color, and materials.

III. Producing the Three-Dimensional Shoe

When the design is complete, the shoe is now ready for manufacturing using a 3D printer. The 3D printer is capable of using a plethora of materials, but also can arrange those materials into various shapes, patterns, weights, etc. The considerations for the various materials to be used include the following:

a. Flexibility/strength: unique blend of different materials can be combined to provide varying degrees of flexibility. A custom shoe would have the ability to exhibit great flexibility where most needed, e.g. where the foot is to pivot or rotate such as the arch and toe joints, and yet provide rigidity in the areas where stiffness is most required for support e.g. base of the heel and around ankle. These can be separate materials that are changed as the part is printed or a single coil of material that has been preloaded with materials of varying flexibility or a dynamic system that is able to blend 2 or more substrates into the desired flexibility on demand.

b. Durability: materials can also be blended to increase strength and ruggedness. This is necessary when making parts of the shoe that will be in contact with the external environment. In particular, the outer sole/tread portion of the shoe that will experience the most wear and tear. Compounds such as hard rubber or plastic can be added to softer materials to increase their hardness resulting in an extended lifetime of the sole. Once again, they can be incorporated as single materials, blends in a single piece or dynamic mixing as the design dictates.

c. Finishes & Coatings: Various methods of treating the raw material or final printed article can be applied to achieve the desired mechanical, physical or optical effect. The following are a non-limiting selection of examples to be mentioned herein:

1. Internal coatings—the areas which directly contact the skin (foot) can be coated with a variety of compounds that would provide a softer second skin feel to the shoe. e.g. felt, fur, wool, man-made fibers, etc.

2. External or internal finishings—the exterior of the shoes can be coated with a variety of compounds that can change the properties of the material for distinct benefits. Examples include:

i) hydrophobic coatings to make waterproof ii) anti-microbial and/or antifungal coatings for bacterial and fungal protection iii) Gore-Tex like coatings to improve breathability and waterproofing iv) Hypoallergenic coating for decreasing skin sensitivity v) Powder finishes or anti-sweat coating for perspiration control vi) Thermochromic finishes or coatings that change color with heat/light vii) Graphene based materials for printing in situ sensors and circuitry directly into the 3D print d. Material Mimicry: The ability to a single or minimum set of materials to achieve desired properties of the entire shoe. Various geometric features and inclusions can be employed to mimic known properties of other materials. examples include the following, but not limited to:

i) Gels—combining air pockets by forming geometric closed structures within the design can emulate the function and form of a gel. Varying the size of the these air pockets either randomly or through a specified pattern can dynamically change the viscoelasticity of the gel providing a tunable scale balancing comfort and support.

ii) Impact absorption—traditional shoe manufacturing techniques employ foams, air pockets, springs, etc. to dampen the transfer of energy from the ground to the person. 3D printed structures in a single, or minimum number of materials, can be design to emulate these characteristics. Features such as coils of varying size and thickness can be employed to change the dampening effect. Sealed or unclosed cavities can be generated to emulate air pockets that also provide dampening.

iii) Tunable structures: Geometric shapes such as, not limited to, triangles, circles, squares, rhombus, spirals, rectangles, etc. can be printed with varying widths, thicknesses and heights as to change the overall physical property of the solid material that is being employed. Such structures and techniques can then be tuned to provide e.g. unique stiffness distributions throughout the shoe or parts of the shoe. Flexibility can be dynamically tuned to accommodate customer need and biometric requirements for foot support in different activity levels e.g. walking, climbing, running etc.

iv) Additives—The inclusion of different additives to the base polymer for various desirable chemical and physical properties, e.g. carbon fibers to improve durability, ceramics for breathability and temperature regulation, particle of gold/silver for antimicrobial and antibacterial activity.

Each shoe design that is dynamic and parametric can be made completely customizable and unique. Various factors of the shoe design will be customizable to include, but not limited to, the following:

a. Basic—wall thickness, colors and ridge details e.g. bumps, waves, grainy, smooth or other 3D TEXTURING capabilities.

b. Interwoven fabrics—e.g. chain mails or joints—custom blend materials, biomechanical mapping with action of feet.

c. Interlocking tab structures for fastening the shoe or different layers.

d. Personalized parametric design features e.g. biomechanical, user input or random generated. The customer will be able to input certain parametric values e.g. Date of Birth, Zodiac sign, pet name, wedding date, anniversary, etc. and mathematically driven algorithms will adapt the core shoe design to reflect a one of a kind extremely personal pattern in the shoe.

e. Mathematical functions to generate unique patterns and fabrics—a single surface or line in and 3D model are generated. To this feature a mathematical function such as e.g. sin-wave, square-wave; Voronio is applied in the GCode to generate patterns that mimic fabrics.

IV. Exemplary System and Method

Figure 15:
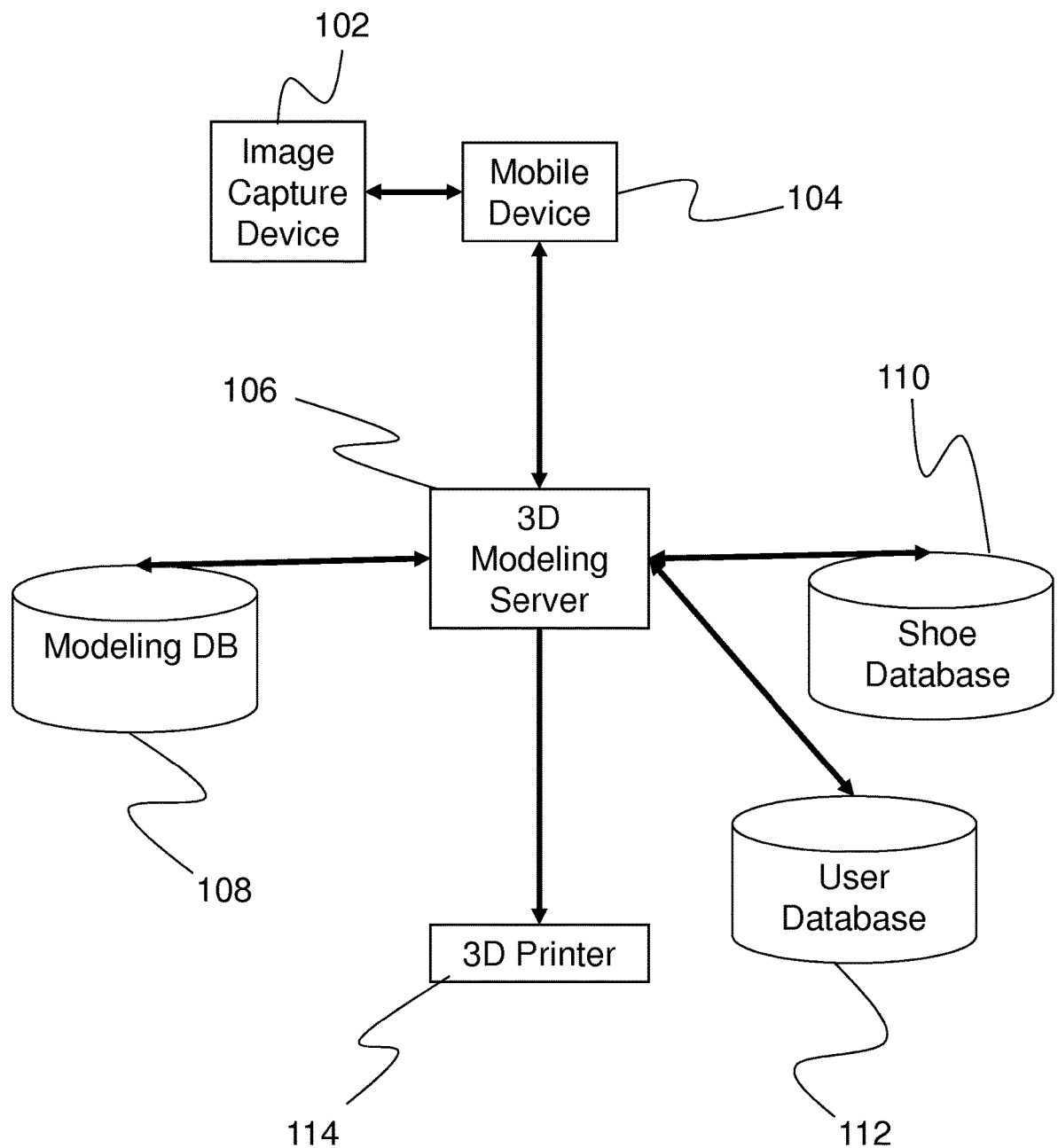
FIG. 15 is a system diagram illustrating a system for creating customized, additive-manufacturers.

One embodiment of a system and method 100 for creating a 3D model of a body part and generating a 3D printed outerwear for the body part is illustrated in FIG. 15. In this embodiment, a user utilizes an image capture device 102, such as a digital camera, and captures several images of a body part from numerous angles (step 202). The captured images are then transmitted to a 3D modeling server 106 from a mobile device 104 connected with or integrated into the digital camera 102. The 3D modeling server 106 accesses a modeling database 108 to render the images into a 3D model (step 204). The 3D model may also be created based on additional user information (step 206), such as a user's physical disability or medical condition which affects their gait, feet, etc. This may include selecting the materials (step 208) and other advanced features for the shoe (step 210), such as specific patterns, shapes, etc. The 3D modeling server may then access the shoe database 110 to provide options for designing a shoe for the foot, at which point the 3D modeling server 106 will communicate with the user via one or more graphical user interfaces displayed on the mobile device 104 (also see FIGS. 17A-H, below). Once the user has selected the desired design, the design is stored in a user database 112, and the 3D modeling server 106 then transmits the design request to a 3D printer 114 for printing the shoe (step 212). As will be described further below, the shoe may also be embedded with one or more sensors, actuators or other electronics (step 214) to obtain usage data or provide the user with therapeutic action. These sensors will be equipped to measure feedback from the use of the shoe (step 216) to determine its effectiveness.

Figure 16:
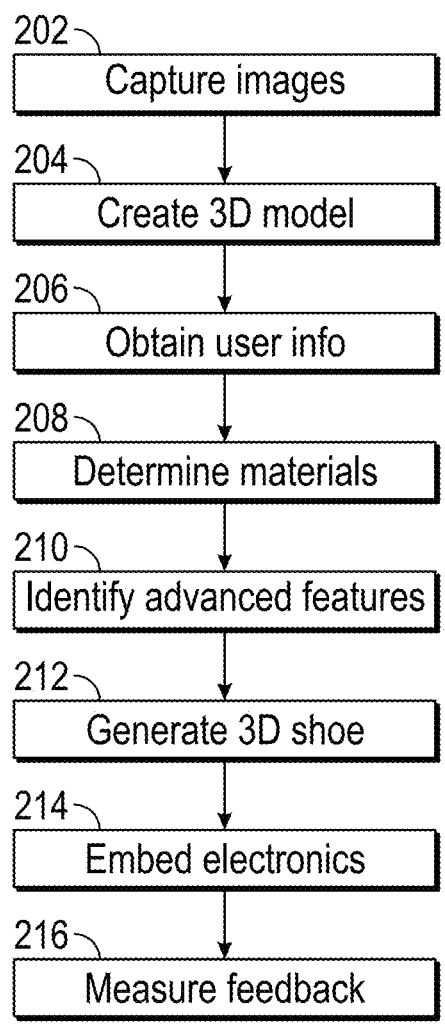
FIG. 16 is a block diagram illustrating a method for creating a 3D model of a foot and generating a 3D shoe based on the model, according to one embodiment.
Figure 19:
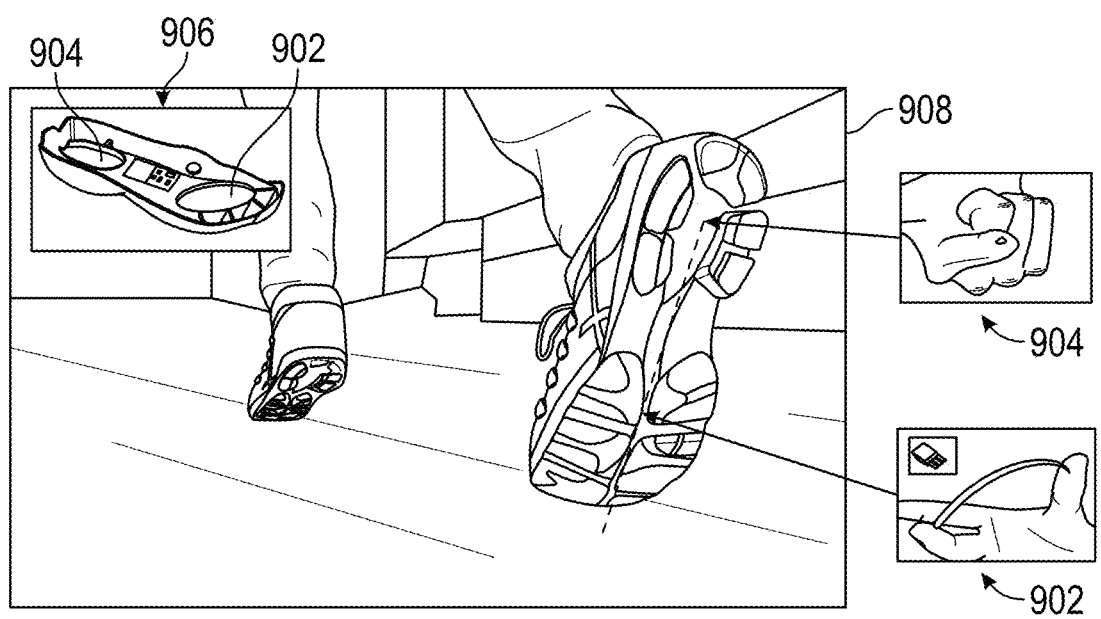
FIG. 19 illustrates embedded electronics in a shoe.

FIG. 16 illustrates a method 200 for creating a 3D model of a body part and generating a 3D printed outerwear for the body part according to some embodiments. In the illustrated example, at operation 202, images are captured, for instance of a user's foot as illustrated in FIG. 1 and described herein. At operation 204, a 3D model is created, for instance a model as illustrated in FIG. 2 and described herein. At operation 206, user information is obtained, for instance via an interactive GUI as depicted in FIGS. 13 and 14 and described herein. At operation 208, materials are determined, for instance based at least in part on user information obtained at operation 206. At an operation 210, advanced features are identified. At operation 212, a 3D shoe is generated, for example by additive manufacturing using a 3D printer. At operation 214, sensors, actuators, or other electronics are embedded, for example embedding one or more weight sensors into a shoe as illustrated in FIG. 19 and described herein. At an operation 216, feedback is measured, for instance from the use of the shoe as described herein.

Figure 17A:
FIGS. 17A-17H illustrate a plurality of graphical user interfaces presented to a user for uploading images to create the 3D model and selecting a 3D printed shoe.
Figure 17B:
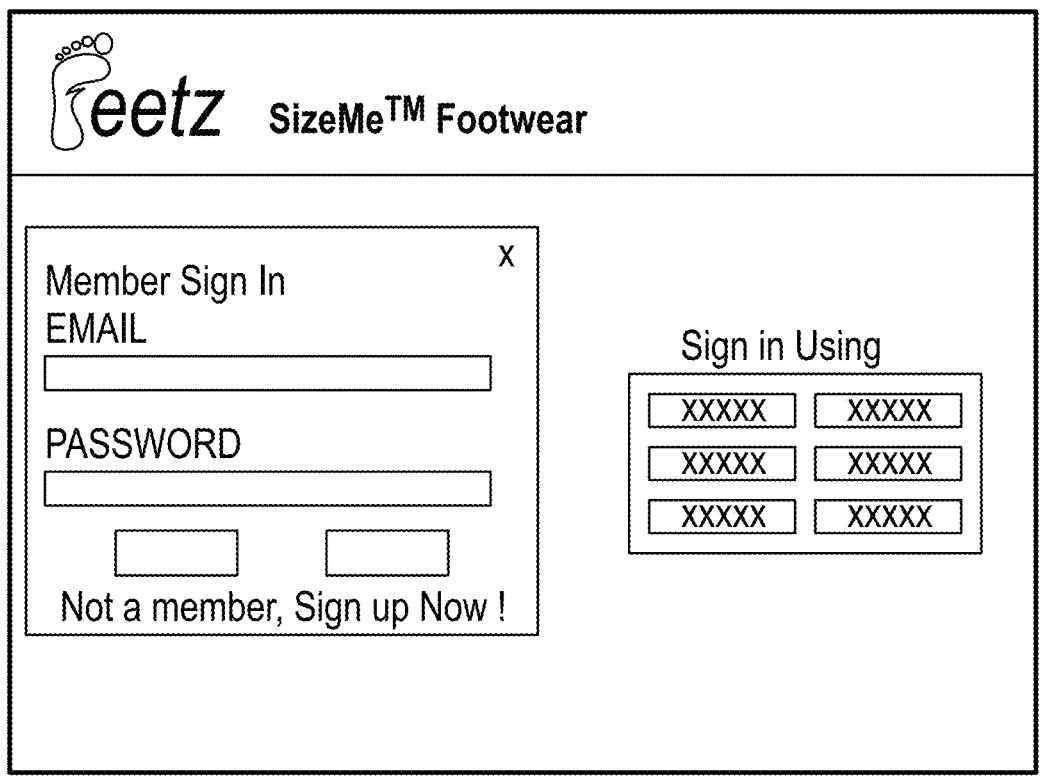
Figure 17C:
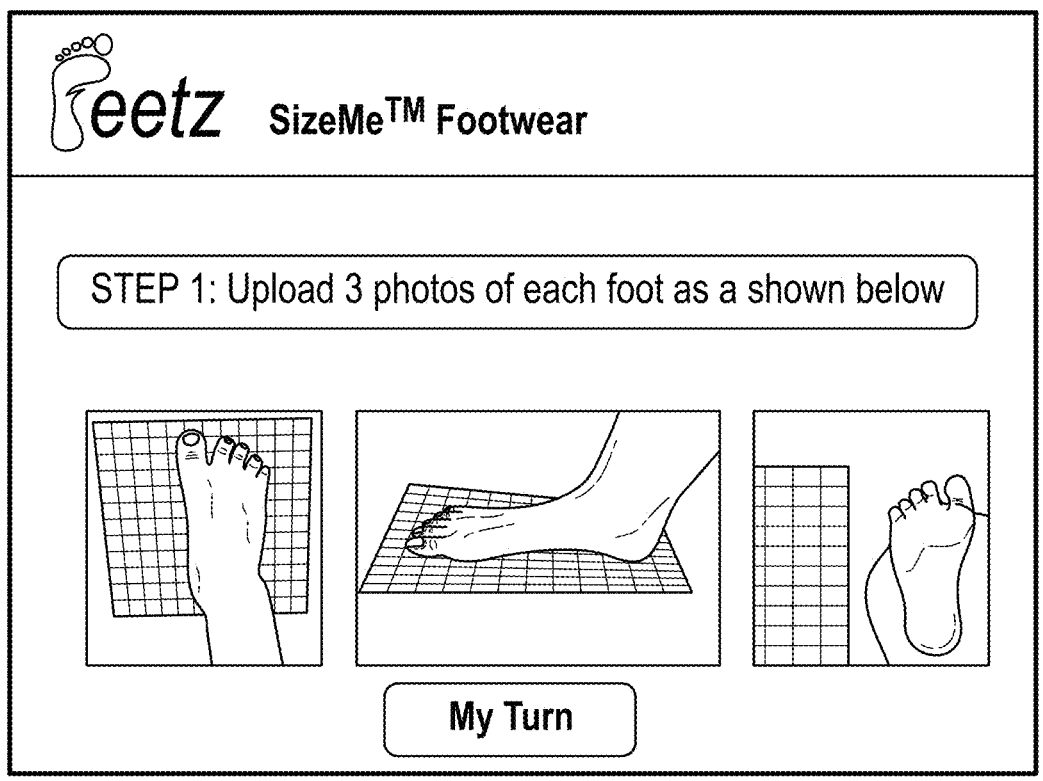
Figure 17D:
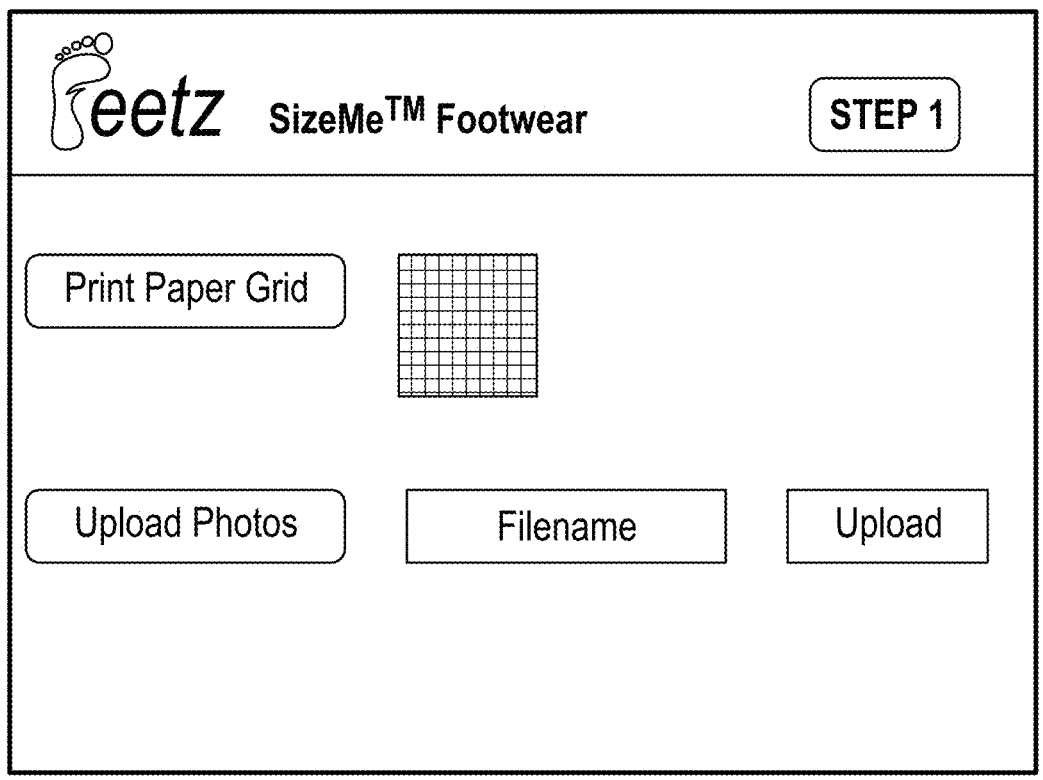
Figure 17E:
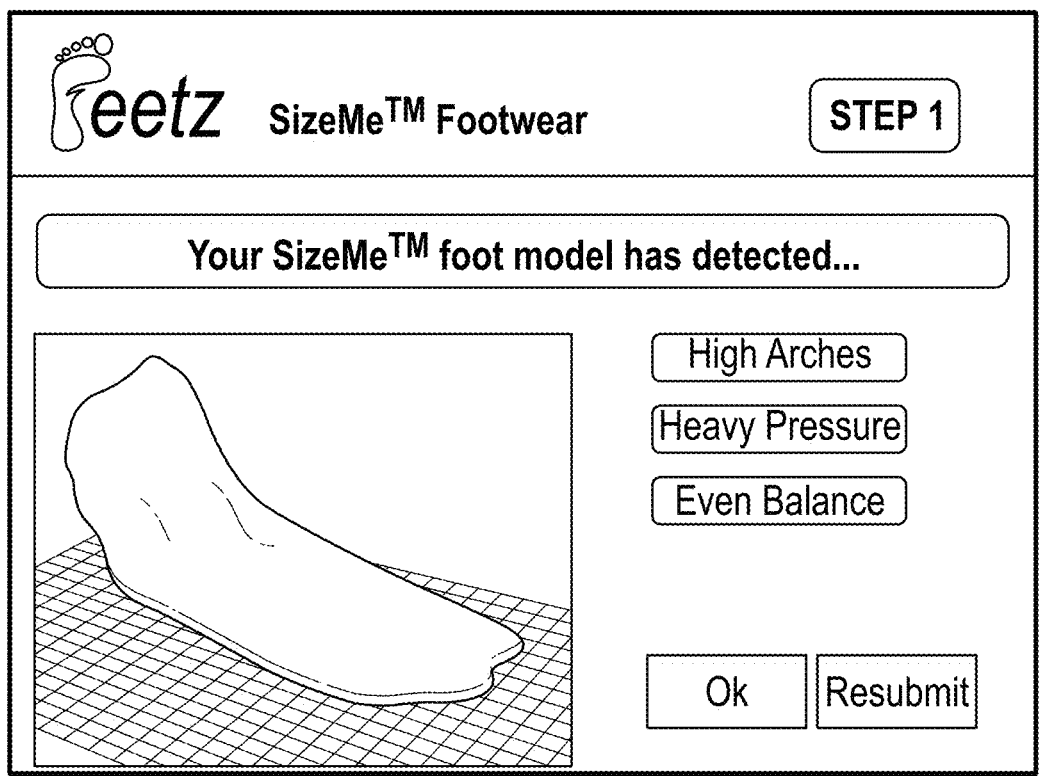
Figure 17F:
Figure 17G:
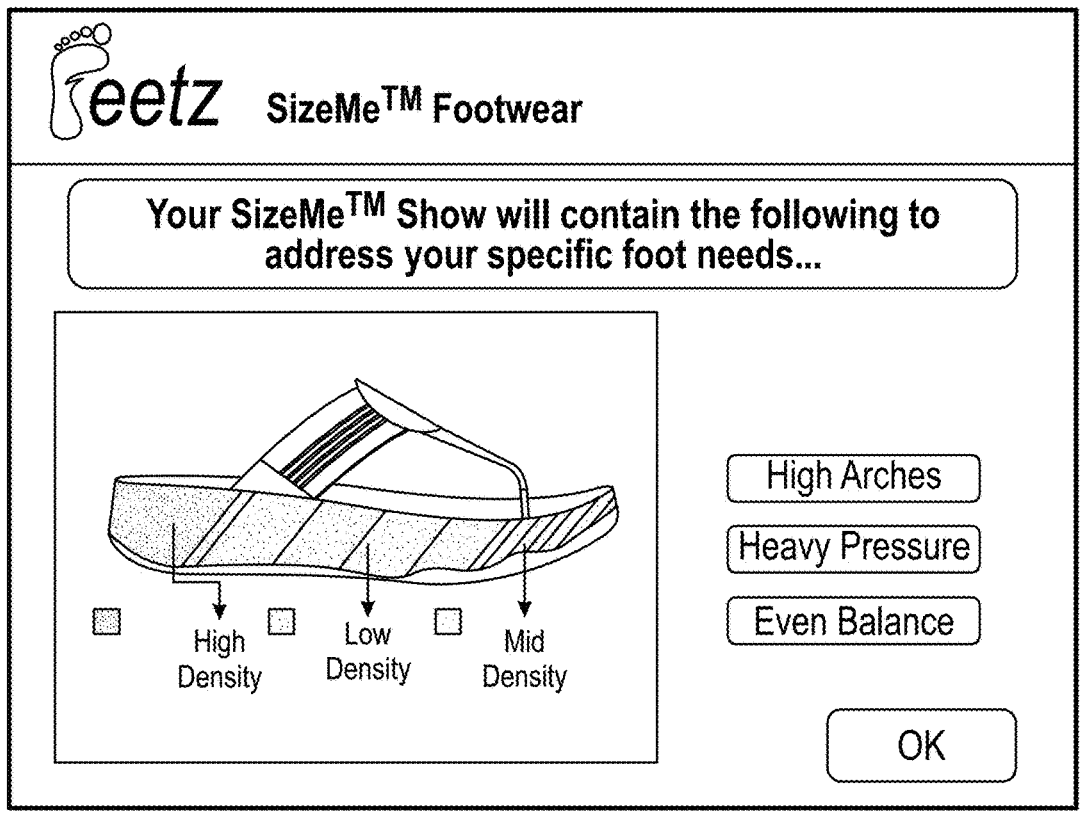
Figure 17H:
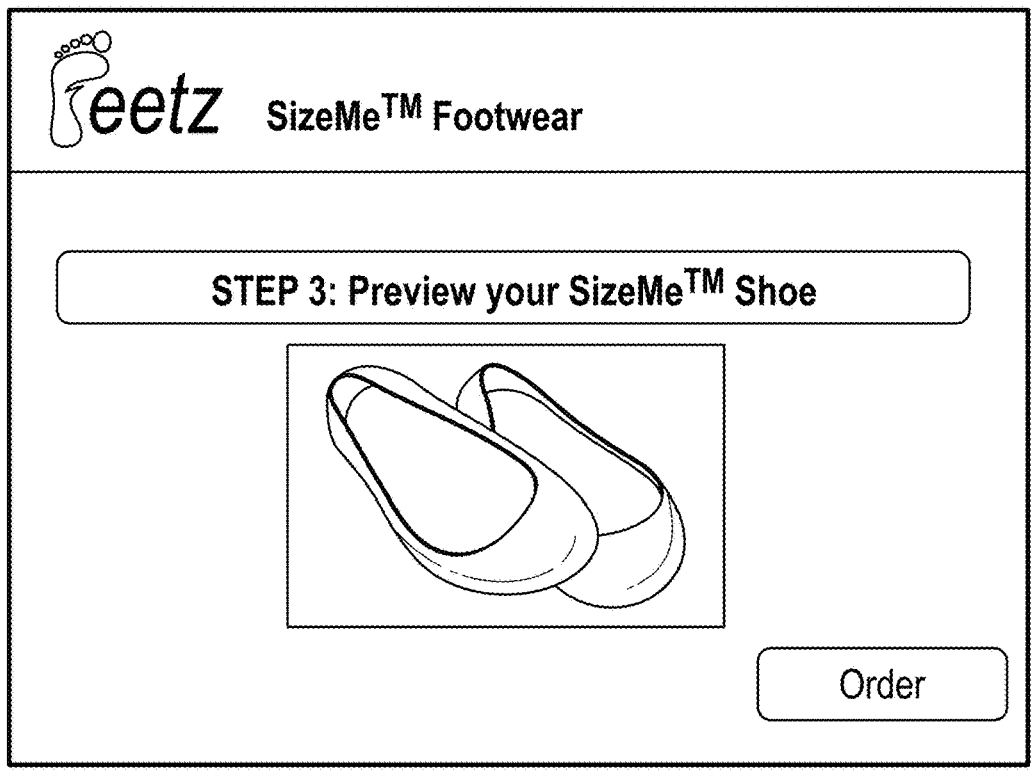

FIGS. 17A-17H illustrate an exemplary GUI that is presented to a user for generating the 3D model and designing and printing a customized shoe. The GUI may be displayed to the user as a webpage hosted by the server 106, or via an application resident on the user's computing device, such as a desktop computer, laptop computer, tablet, mobile device or other computing device. As shown in FIGS. 17A-17H, the user can log in, receive instructions on capturing images of a body part (in this case, the foot), including printing paper grids. The user is then directed to upload their photos, after which the 3D modeling server utilizes the pictures to render the 3D model, as shown in FIG. 17E. The GUI may provide a preliminary indication based on an initial analysis of the shape of the foot as to whether the user suffers from high arches or heavy pressure. The user may then continue to select a size, style, etc., after which the user is presented with an image of the resulting shoe and the features that the shoe provides—likely the features identified by the system as lacking based on the 3D model.

V. Sensors and Intelligence

In addition to features that would apply increased pressure to the specified zone, additional sensors/thermocouples could be inserted into the shoes to apply heat at the same time. Piezo elements or small sonication devices could be included to provide vibrational patterns to improve massaging. Also, electrodes could be inserted into the soles that make contact with the skin to provide electronic stimulation of the muscles in the foot for injury therapy.

Activation/massaging of different area could be achieved by either printing interchangeable insoles that targeted specific areas e.g. kidneys, eyes, stomach etc. and user would swap out based on their particular needs. Or, inflatable pockets connected by microfluidic structures could be activated either by gas or liquid that would expand into the pressure point activating that area and dynamically change with software driven by an internal CPU, smart phone, laptop or other wireless/Bluetooth connected controller device.

Microfluidics—A method of creating channels within the shoe can be employed that allow for additional fluid based mechanics to be employed in the shoe, examples include but not limited to:

Light/Luminescence—fluorescence within the channels that will react based on light (e.g. for night walking safety), on a specific action by the user (e.g. highlights when a user rolls their foot over a 45 degree angle that will create a correction of the walking gait)

Fluids—channels can contain fluids to perform actions needed by the users that include adjusting to impact/creating resistance to impact (i.e. dropping a heavy object on the foot can create an air bag style simulation on the toe), shock absorbency, regulated via pressure from the foot, oscillation of the fluids with a user driven button to create a massage effect to improve blood flow Material change—channels can change with the foot to changes in the fit of the shoe throughout the period it is worn, e.g. the foot expands up to 5% within the day and the shoe can shrink with the use of the dynamic channels to remain a comfortable fit.

Figure 21:
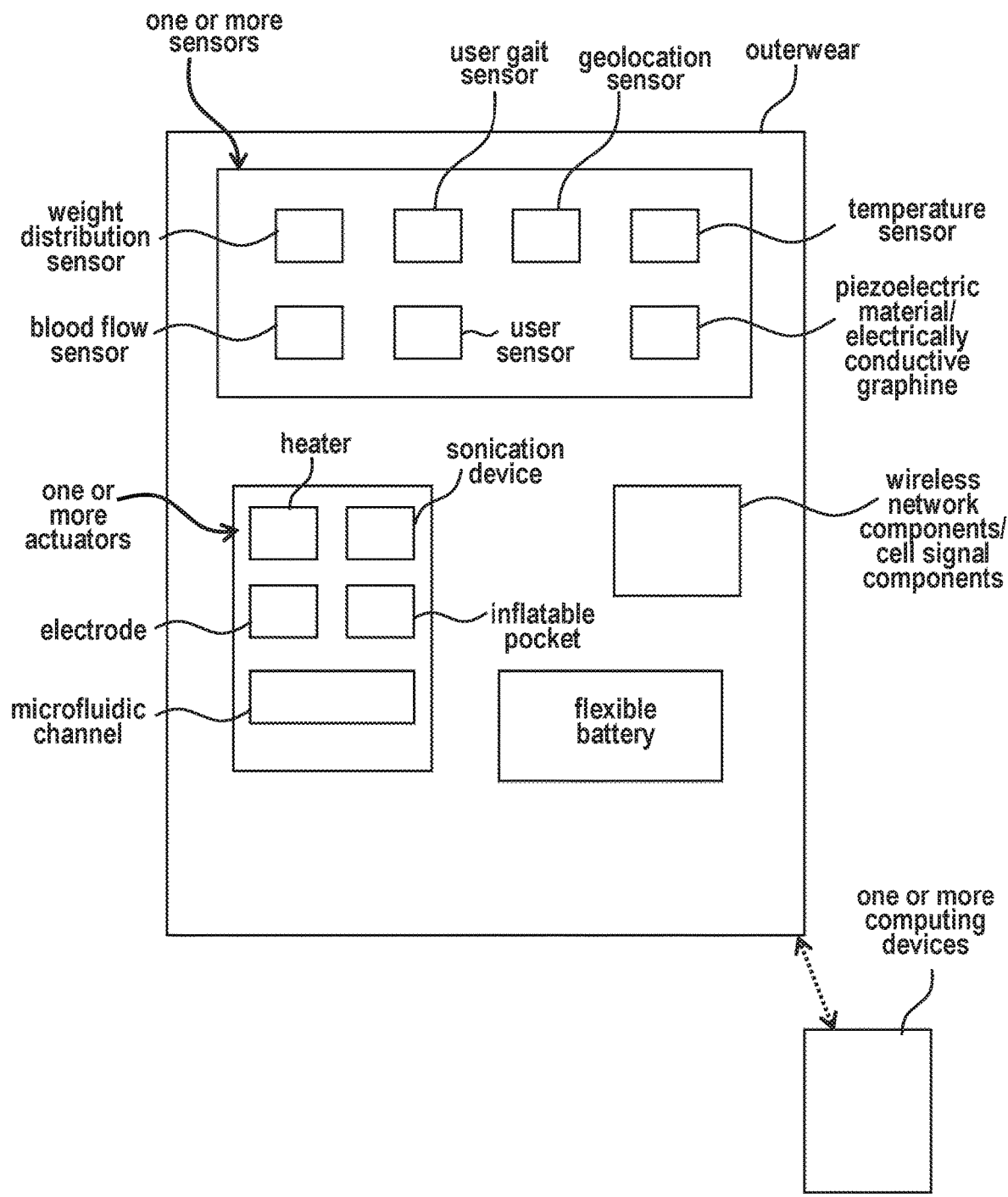
FIG. 21 illustrates sensors, actuators, wireless network components/cell signal components, and a flexible battery embedded in outerwear.

Wearable Sensors—Additional sensors could be added or 3d printed into the shoe to allow for a variety of additional features. The sensors can either be off-the-shelf and embedded into the design of the shoe, or use materials that are actually electrically conductive e.g. graphene based, that will be able to print the circuits and sensors directly into shoe design. Examples of such embedded tech are illustrated in FIG. 19. For example, FIG. 19 illustrates electronic technology 902, 904 embedded in an insole 906 or sole 908 of a shoe. Such embedded tech may be and/or include flexible electronics, near field charging equipment, wireless integration components, nine axis gyroscopic sensors through LTE, and/or other embedded tech. Examples of sensors that could be added or 3D printed into the shoe to allow for a variety of additional features are, but not limited to:

a) weight distribution, embedded sensors that detect the users weight and outputs a distribution of that weight across both feet and surface area of the feet.

b) measuring gait—embedded sensors that detect and monitor a user's gait, do they lead heel toe or reverse, do they favor one foot over the other, pronation, etc.

c) time lapse or recovery monitoring—utilizing embedded sensors for real time tracking of correction of existing issues.

d) Automatic nightlights—lights that are embedded within the shoes that are light sensor activated, motion or impact activated.

e) GPS—embedded sensor for location, pedometer, speed distance, etc.

f) weight tracking—real time monitoring of users weight, can be connected to an app.

g) Automatic "Replace-Me" sensor, i.e. your shoes are no longer providing you the support you need.

h) Near-field charging (wireless charging) through embedded flexible batteries allowing charging of electronic functions and sensors without physical connection to an external power source.

i) Wi-Fi and cell signal capabilities through embedded chips such as LTE or other cellphone based chips, permitting the transfer of data from sensor based activities to cloud, apps or other data collecting methods FIG. 21 illustrates sensors, actuators, wireless network components/cell signal components, and a flexible battery embedded in outerwear.

VI. Applications

Growth Prediction model: e.g. for Children's footwear. Children's feet grow at extremely fast rates. Mathematical models can be employed based on some input data that would allow us to predict the growth pattern of the child's feet and print a pair of shoes to match this growth rate that can be generated as kids feet grow. Automatically predict growth and have ready & printed Health Prediction model: Employing examples outlined previously (e.g. weight, gait, blood flow) allows for data collection to create a prediction of common health issues (e.g. diabetes indicator with a deterioration of blood flow, gout with a swelling seen in the foot). This data can be used to indicate to the user to see a medical expert for diagnosis and the data can be sent to the medical expert in assistance in diagnosis.

Figure 20:
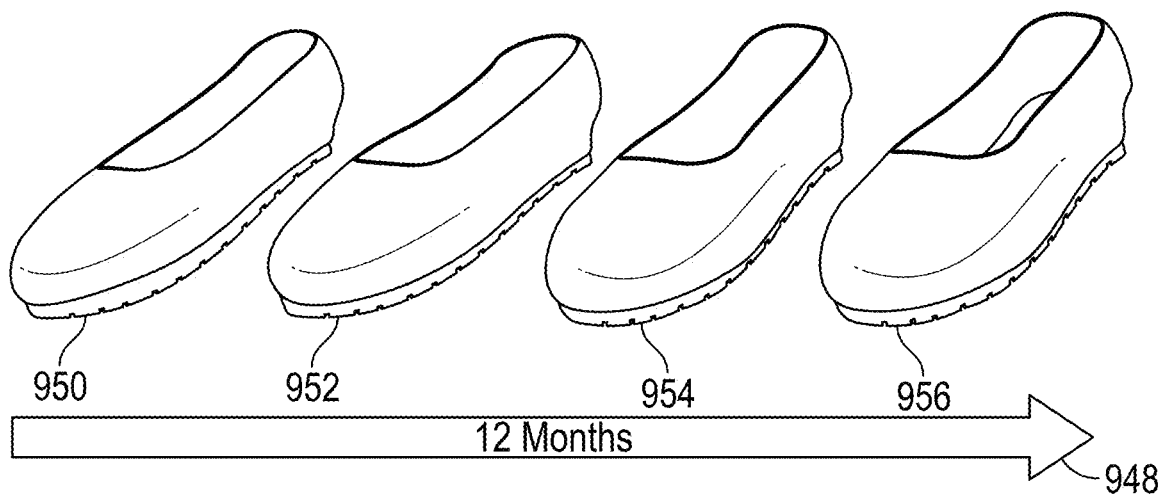
FIG. 20 illustrates additively manufactured orthotics.

Corrective orthotic issues e.g. supination, pronation, gait alignment, surgery recovery etc. Individuals seek medical assistance for a variety of foot conditions that cause discomfort. The standard method of providing support for these issues is an orthotic that is created with the aid of a medical practitioner. This is in the form of a single orthotic that tries to correct the issue. Here we present the idea of creating a more gradual correction using a selection of 3D printed shoes that correct the issue overtime and can be monitored using the embedded sensor technology. This is shown in FIG. 20. FIG. 20 illustrates a selection of 3D printed shoes 950, 952, 954, 956 that correct the issue over time 948.

VII. Computer-Enabled Embodiment

FIG. 18 is a block diagram illustrating an example wired or wireless system 550 that may be used in connection with various embodiments described herein. For example the system 550 may be used as or in conjunction with a system for modeling a body part and designing a 3D printable object, as previously described with respect to FIGS. 1-17H. The system 550 can be a conventional personal computer, computer server, personal digital assistant, smart phone, tablet computer, or any other processor enabled device that is capable of wired or wireless data communication. Other computer systems and/or architectures may be also used, as will be clear to those skilled in the art.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

System 550 preferably includes a main memory 565 and may also include a secondary memory 570. The main memory 565 provides storage of instructions and data for programs executing on the processor 560. The main memory 565 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 570 may optionally include a internal memory 575 and/or a removable medium 580, for example a floppy disk drive, a magnetic tape drive, a compact disc ("CD") drive, a digital versatile disc ("DVD") drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 570. Examples of external storage medium 595 may include an external hard disk drive or an external optical drive, or and external magneto-optical drive.

Other examples of secondary memory 570 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage media 580 and communication interface 590, which allow software and data to be transferred from an external medium 595 to the system 550.

System 550 may also include an input/output ("I/O") interface 585. The I/O interface 585 facilitates input from and output to external devices. For example the I/O interface 585 may receive input from a keyboard or mouse and may provide output to a display. The I/O interface 585 is capable of facilitating input from and output to various alternative types of human interface and machine interface devices alike.

System 550 may also include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a modem, a network interface card ("NIC"), a wireless data card, a communications port, a PCMCIA slot and card, an infrared interface, and an IEEE 1394 fire-wire, just to name a few.

Communication interface 590 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

The system 550 also includes optional wireless communication components that facilitate wireless communication over a voice and over a data network. The wireless communication components comprise an antenna system 610, a radio system 615 and a baseband system 620. In the system 550, radio frequency ("RF") signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit ("IC"). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown) that are executable by processor 560.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. A diagnostic and therapeutic outerwear system, the system comprising:
   a processor configured to facilitate:
      receiving one or more images of a portion of a body of a user;
      creating a three-dimensional (3D) model of the portion of the body of the user based at least in part on the one or more images;
      determining at least one material suitable for additive manufacturing of an outerwear configured to be worn on the portion of the body of the user; and
      generating, using an additive manufacturing process, the outerwear made at least in part from the at least one material, wherein the outerwear is formed to provide a custom fit, based on the 3D model, to the portion of the body of the user where the outerwear is worn;
   one or more sensors embedded within the outerwear, the one or more sensors configured to generate diagnostic output signals that convey information related to one or more of physical activity of the user or physiological information of the user, the diagnostic output signals communicated to one or more computing devices; and
   one or more actuators embedded within the outerwear, the one or more actuators configured to provide therapy to the user, the actuators controlled by the one or more computing devices to provide the therapy based on the diagnostic output signals,
   wherein, the processor is further configured to facilitate:
      forming the one or more sensors and the one or more actuators integrally in the outerwear during additive manufacturing; and
      forming interlocking tabs and holes in the outerwear during additive manufacturing for locking the one or more sensors and the one or more actuators to the outerwear such that the one or more sensors and the one or more actuators are embedded therein.

2. The system of claim 1, wherein at least one of the one or more actuators comprises a device selected from the group consisting of a heater, a sonication device, an electrode, an inflatable pocket, and a microfluidic channel that responds to pressure applied to the channel by the user.

3. The system of claim 2, wherein at least one of the one or more actuators is configured such that the therapy provided to the user is selected from the group consisting of electronic muscle stimulation, heat therapy provided to the portion of the body of the user, pressure massaging provided to the portion of the body of the user, and vibrational massaging provided to the portion of the body of the user.

4. The system of claim 1, wherein at least one of the one or more sensors is selected from the group consisting of a weight distribution sensor, a user gait sensor, a geolocation sensor, a temperature sensor, and a blood flow sensor.

5. The system of claim 1, wherein the one or more sensors include one or more of a piezoelectric material, or an electrically conductive graphene based material printed directly into the outerwear.

6. The system of claim 1, wherein the one or more sensors include a weight sensor and a gait sensor.

7. The system of claim 1, wherein the one or more actuators further comprise at least one microfluidic channel in the outerwear.

8. The system of claim 1, wherein the one or more sensors and the one or more actuators are embedded with the outerwear in one or more locations that are determined based on user information including information related to one or more of a physical activity level of the user, a disability of the user, an age of the user, biomechanical information about the user, or a physical history of the user.

9. The system of claim 1, wherein the outerwear is a shoe, and wherein a weight distribution of the user in the shoe is determined by the one or more computing devices based on the output signals.

10. The system of claim 1, wherein the one or more sensors are coupled with flexible batteries embedded in the outerwear configured for near-field charging without physical connection to an external power source; and wherein the one or more sensors are coupled with wireless network components and/or cell signal components embedded in the outerwear and configured to facilitate transfer of data from the one or more sensors to cloud storage and/or electronic applications.

11. The system of claim 1, wherein the outerwear is a selection of three-dimensional (3D) printed shoes that correct orthotic issues over time.

12. A method for forming diagnostic and therapeutic outerwear, the method comprising:

receiving one or more images of a portion of a body of a user;

creating a three-dimensional (3D) model of the portion of the body of the user based at least in part on the one or more images;

determining at least one material suitable for additive manufacturing of an outerwear configured to be worn on the portion of the body of the user;

generating, using an additive manufacturing process, the outerwear made at least in part from the at least one material, wherein the outerwear is formed to provide a custom fit, based on the 3D model, to the portion of the body of the user where the outerwear is worn;

generating, with one or more sensors embedded within the outerwear, diagnostic output signals that convey information related to one or more of physical activity of the user or physiological information of the user, the diagnostic output signals communicated to one or more computing devices;

providing, with one or more actuators embedded within the outerwear, therapy to the user, the actuators controlled by the one or more computing devices to provide the therapy based on the diagnostic output signals, and forming the one or more sensors and the one or more actuators integrally in the outerwear during additive manufacturing and forming interlocking tabs and holes in the outerwear during additive manufacturing for locking the one or more sensors and the one or more actuators to the outerwear such that the one or more sensors and the one or more actuators are embedded therein.

13. The method of claim 12, wherein at least one of the one or more actuators comprises a device selected from the group consisting of a heater, a sonication device, an electrode, an inflatable pocket, and a microfluidic channel that responds to pressure applied to the channel by the user.

14. The method of claim 13, wherein the therapy provided to the user is selected from the group consisting of electronic muscle stimulation, heat therapy provided to the portion of the body of the user, pressure massaging provided to the portion of the body of the user, and vibrational massaging provided to the portion of the body of the user.

15. The method of claim 12, wherein at least one of the one or more sensors is selected from the group consisting of a weight distribution sensor, a user gait sensor, a geolocation sensor, a temperature sensor, and a blood flow sensor.

16. The method of claim 12, wherein the one or more sensors include one or more of a piezoelectric material, or an electrically conductive graphene based material printed directly into the outerwear.

17. The method of claim 12, further comprising generating the diagnostic output signals using at least a weight sensor and a gait sensor.

18. The method of claim 12, further comprising providing the therapy using at least one microfluidic channel in the outerwear.

19. The method of claim 12, further comprising embedding the one or more sensors and the one or more actuators with the outerwear in one or more locations that are determined based on user information including information related to one or more of a physical activity level of the user, a disability of the user, an age of the user, biomechanical information about the user, or a physical history of the user.

20. The method of claim 12, wherein the outerwear is a shoe, the method further comprising determining a weight distribution of the user in the shoe with the one or more computing devices based on the output signals.

21. The method of claim 12, wherein the one or more sensors are coupled with flexible batteries embedded in the outerwear configured for near-field charging without physical connection to an external power source; and wherein the one or more sensors are coupled with wireless network components and/or cell signal components embedded in the outerwear and configured to facilitate transfer of data from the one or more sensors to cloud storage and/or electronic applications.

22. The method of claim 12, wherein the outerwear is a selection of three-dimensional (3D) printed shoes that correct orthotic issues over time.

* * * * *